(12) United States Patent
Greer

(10) Patent No.: US 6,933,287 B1
(45) Date of Patent: Aug. 23, 2005

(54) DRAMATIC SIMPLIFICATION OF A METHOD TO TREAT NEOPLASTIC DISEASE BY RADIATION

(76) Inventor: Sheldon B. Greer, 3600 Mystic Pointe Dr., LPH9, Aventura, FL (US) 33180

( * ) Notice: Subject to any disclaimer, the term of this patent is extended or adjusted under 35 U.S.C. 154(b) by 0 days.

(21) Appl. No.: 09/514,278

(22) Filed: Feb. 28, 2000

Related U.S. Application Data

(60) Provisional application No. 60/122,479, filed on Mar. 1, 1999.

(51) Int. Cl.$^7$ ............................................. A61K 31/70
(52) U.S. Cl. ...................................................... 514/49
(58) Field of Search .......................................... 514/49

(56) References Cited

U.S. PATENT DOCUMENTS

| | | | | |
|---|---|---|---|---|
| 4,894,364 A | | 1/1990 | Greer | ........................... 514/49 |
| 5,985,266 A | | 11/1999 | Link, Jr. et al. | ......... 424/93.21 |

FOREIGN PATENT DOCUMENTS

| | | |
|---|---|---|
| WO | WO 85/01871 | 5/1985 |
| WO | WO 96/26743 | 9/1996 |

OTHER PUBLICATIONS

Greer et al., Int. J. Ratiat. Oncol., Biol., Phys. (1992), 22(3), 505–10 Abstract Only.*

Santos, O, Perez, L, Briggle, T, Boothman, D, Greer, S. 1990. Radiation, pool size and incorporation studies in mice with 5-chloro-2'-deoxycytidine. *Int. J. Radiat. Oncol. Biol. Phys.* 19:357–365.

Greer, S, Santos, O, Gottlieb, C, Schwade, J., Marion, S. 1990. 5–Chlorodeoxycytidine, a radiosensitizer effective against RIF–1 and Lewis lung carcinoma, is also effective against a DMBA–induced mammary adenocarcinoma and the EMT–6 tumor in BALB/c mice. *Int. J. Rad. Oncol. Biol. Phys.* 22:505–510.

Greer, S, Schwade, J, Marion, S. 1995. Five–chlorodeoxycytidine and biomodulators of its metabolism result in fifty to eighty percent cures of advanced EMT–6 tumors when used with fractionated radiation. *Int. J. Rad. Oncol. Biol. Phys.* 32:1059–1069.

Kim, C–H., Marquez, V., Mao, D., Haines, D., McCormack, J. 1986. Synthesis of pyrimidin–2–one nucleoside as acid–stable inhibitors of cytidine deaminase. *J. Med. Chem* 29:1374–1380.

Marquez, V. 1994. Inhibition of cytidine deaminase: mechanism and effects of the metabolism of antitumor agents. In: *Developments in Cancer Chemotherapy*, Robert I. Glazer, ed, CRC Press, Boca Raton, FL, pp. 92–114.

Kelly, J., Driscoll, J., McCormack, J., Roth, J., Marquez, V. 1986. Furanose–pyranose: isomerization of reduced pyrimidine and cyclic urea ribosides. *J. Med. Chem.* 29:2351–2358.

Wempen, I., Duschinsky, R., Kaplan, L., and Fox, J. 1961. Organic and biological chemistry. Thiation of Nucleosides. IV. The synthesis of 5–fluoro–2'–deoxycytidine and related compounds. *J. Amer. Chem. Soc.* 83:4755–4766.

Russell, K., Rice, G., Brown, J. 1986. In vivo and in vitro radiation sensitization by the halogenated pyrimidine 5–chloro–2'–deoxycytidine. *Cancer Res.* 46:2883–2887.

Kinsella, T., Kunugi, K., Vielhuber, K., McCulloch, W., Liu, S–H., and Cheng, Y–C. 1994. An in vivo comparison of oral 5–Iodo–2'–deoxyuridine and 5–iodo–2–pyrimidinone–2'doexyribose toxicity, pharmacokinetics, and DNA incorporation in athymic mouse tissues and the human colon cancer xenograft, HCT–116. *Cancer Res.* 54:2695–2700.

Wataya, Y., Santi, D., Hansch, C. 1977. Inhibition of *Lactobacillus casei* thymidylate synthetase by 5–substituted 2'–deoxyuridylates. Preliminary quantitative structure–activity relationship. *J. Med. Chem.* 20: 1469–1473. In: Balzarini, J., DeClerq, E., Mertes, M., Shugar, D., Torrence, P. 1982. 5–Substituted 2'–deoxyuridines: Correlation between inhibition of tumor cell growth and inhibition of thymidine kinase and thymidylate synthetase. *Biochem. Pharmacol.* 31:3673–3682.

Wataya, Y., Santi, D. 1975. Thymidylate synthetase catalyzed dehalogenation of 5–bromo– and 5–iodo–2'–deoxyuridylate. *Biochem. Biophys. Res. Commun.* 67:818–823.

Caradonna, S, Cheng, Y–C. 1980. The role of deoxyuridine triphosphate nucleotidohydrolase, uracil–DNA glycosylase, and DNA polymerase α in the metabolism of FUdr in human tumor cells. *Mol. Pharmacol.* 18:513–520.

Hirota, Y, Yoshioka, A, Tanaka, S, et al. 1989. DNA double–strand breaks, and cell death caused by 2–chlorodeoxyadenosine in mouse FM3A cells. *Cancer Res.* 49:915–919.

Jones, P, Taylor, S. 1980. Cellular differentiation, cytidine analogs, and DNA methylation. *Cell.* 20:85–93.

Kaysen, J, Spriggs, D, Kufe, D. 1986. Incorporation of 5–fluorodeoxycytidine and metabolites into nucleic acids of human MCF–7 breast carcinoma cells. *Cancer Res.* 46:4534–4538.

Osterman, D., DePillis, G., Wu, J. Matsuda, A., Santi, D.1988. 5–Fluorocytosine in DNA is a mechanism–based inhibitor of HhaI methylase. *Biochemistry.* 27:5204–5210.

Yang, A,. Shen, J–C, Zingg, J–M, Jones P. 1995. HhaI and HpaII DNA methyltransferase bind DNA mismatches, methylate uracil and block DNA repair. *Nucl. Acids Res.* 23:1380–1387.

(Continued)

*Primary Examiner*—Rebecca Cook
(74) *Attorney, Agent, or Firm*—Rothwell, Figg, Ernst & Manbeck, P.C.

(57) ABSTRACT

A method of treating tumors with radiation is disclosed, wherein the tumor is sensitized by administering a tumor sensitizing agent comprising 5-chloro-2'-deoxycytidine, 4-N-methyl FdC and a cytidine deaminase inhibitor to a patient having the tumor. The tumor is then subjected to radiation.

20 Claims, 3 Drawing Sheets

OTHER PUBLICATIONS

Figure 1A:
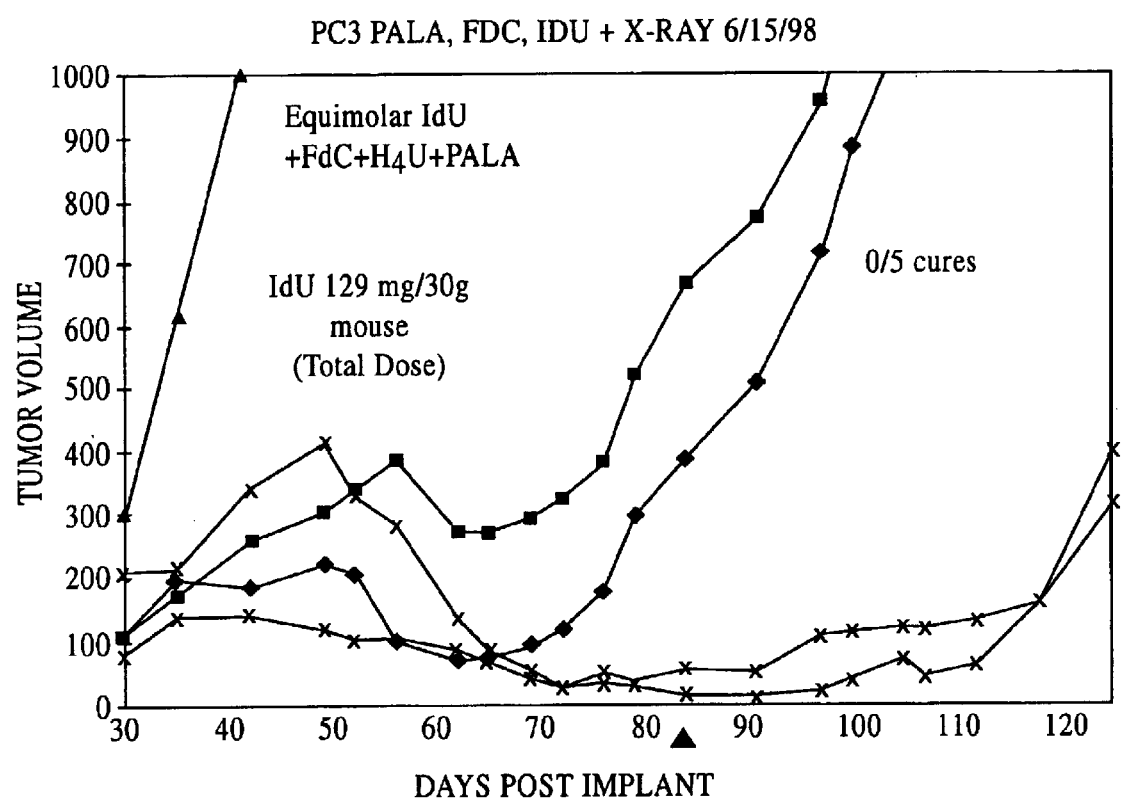
Figure 1B:
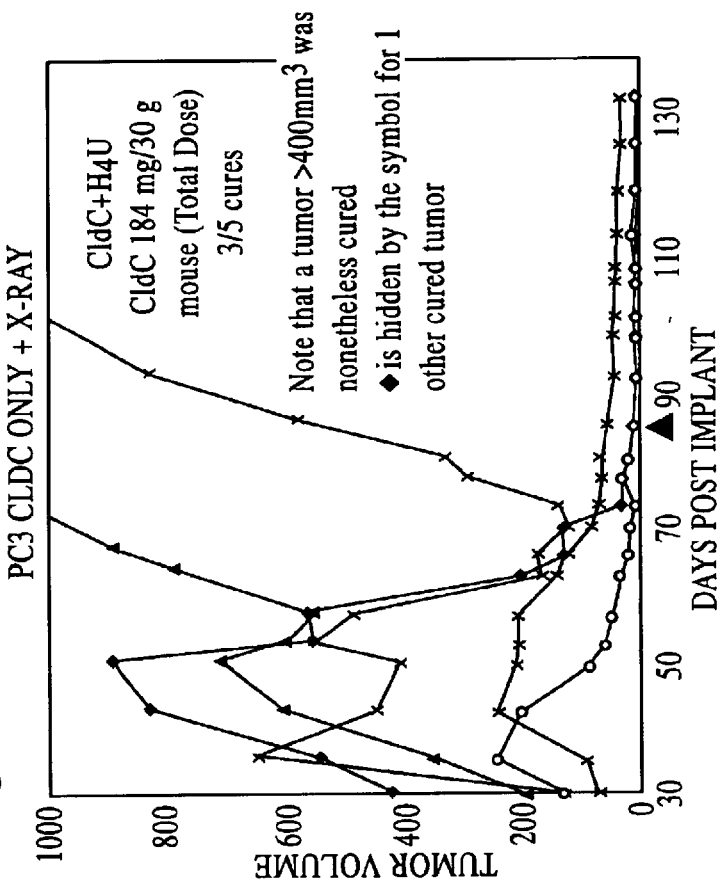
Figure 1C:
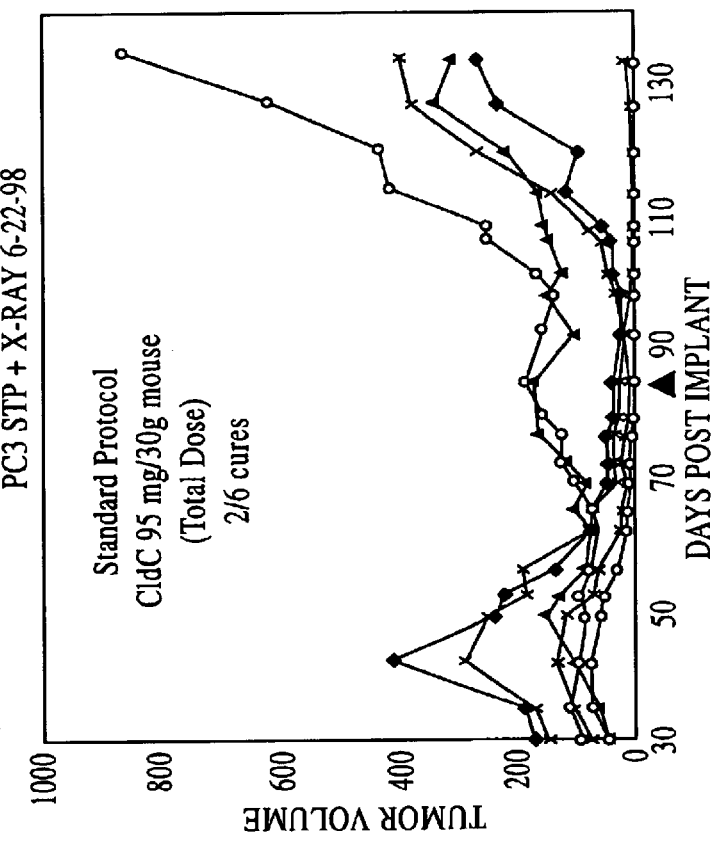

Jones, P, Rideout, W.,III, Shen, J–C, et al. 1992. Methylation, mutation and cancer. *BioEssays.* 4:33–36.

El–Deiry, W., Nelkin, B., Celano, P., Yen, C., Falco, J., Hamilton, S., Baylin, S. 1991. High expression of the DNA methyltransferase gene characterizes human neoplastic cells and progression stages of colon cancer. *Proc. Natl. Acad. Sci. USA.* 88:3470–3474.

Baylin, S. and Herman, J. 2000. Promoter hypermethylation and gene silencing in cancer. *Advances in Gene Tech: DNA, RNA and Cancer.* Miami Nature Biotechnology Winter Symposium, p. 43.

Wollner et al. Abstract, "Toxicity of Hepatic Arterial 5 Bromo–2'–Deoxyuridine Followed by Yttrium–90 Microspheres in Dogs", Proc. Am. Soc. Clin. Oncol. Annu. Meet., May 4–6, 1986, vol. 5, p. 46.

Boothman et al. Abstract, "Potentiation of Halogenated Pyrimidine Radiosensitizers in Human Carcinom Cells by Beta.–1apachone(3,4–dihydro–2, 2–dimethyl–2H–naphtho'1,2–b!pyra 5,6–dione), a Novel DNA Repair Inhibitor", Cancer Res. (1987), vol. 47, pp. 5361–5366.

Perez et al. Abstract, "Marked Radiosensitization of Cells in Culture to X–Ray by 5–chlorodeoxycytidine Coadministered with Tetrahydrouridine, and Inhibitors of Pyrimidine Biosynthesis", Int. J. Radiat. Oncol., Biol., Phys., (1984), vol. 10, pp. 1453–1458.

Zucchetti et al. Abstract, "Temozolomide–Induced Differentiation of K562 Leukemia Cells is not Mediated by Gene Hypomethylation", Biochem. Pharmacol. (1989), vol. 38, pp. 2069–2075.

Mundinger et al. Abstract, "Post–Operative Stereotactic Curie–Therapy Using the Iridium–192 GammaMed Contact Irradiation Apparatus Combined with Radio–Sensitizers in Treating Multiform Glioblastomas", ACTA Neurochirurgica, vol. 42, pp. 73–77 (1978).

Greer et al. Abstract, "5–Chlorodeoxycytidinie, a Radiosensitizer Effective Against RIF–1, and Lewi Lung Carcinoma, is Also Effective Against a DMBA–Induced Mammary Adenocarcinoma and the EMT–6 Tumor in BALB/c Mice", Int. J. Radiat. Oncol., Biol., Phys. (1992), vol. 22, pp. 505–510.

Kalinich et al. Abstract, "Radioprotective Properties of DNA Methylation–Disrupting Agents", International Journal of Radiation Biology, (1991), vol. 59, pp. 1217–1226.

Thibault et al. Abstract, "A Phase II Study of 5–aza–2'deoxycytidine (decitabine) in Hormone Independent Metastatic (D2) Prostate Cancer", http://www.Oncolink.Com Cancernet/98/Aug/708471.HTML&50, Tumori, vol. 84, pp. 87–89 (1998).

Lawrence et al. Abstract, "Selective Radiosensitization and Cytotoxicity of Human Melanoma Cells using Halogentated Deoxycytidines and Tetrahydrouridine Retrieved from STN", Int. J. Radiat. Oncol. Biol. Phys. (1989). pp. 1243–1246.

* cited by examiner

DRAMATIC SIMPLIFICATION OF A METHOD TO TREAT NEOPLASTIC DISEASE BY RADIATION

This application claims the benefit of U.S. Provisional Application No. 60/122,479, filed Mar. 1, 1999.

FIELD OF THE INVENTION

The present invention is related to agents useful in the treatment of tumors by radiation by sensitizing tumor cells toward the radiation. The invention is also related to a method of treating tumors by administering the agents before and/or during a course of radiation treatment. The agents can perform selective tumor radiosensitization. The agents are also involved in tumor directed hypomethylation. The agents of the invention include 5-chloro-2'-deoxycytidine (Cytochlor or CldC) administered with a cytidine deaminase inhibitor (Tetrahydrouridine ($H_4U$) or Zebularine (Zb), for example) or CldC administered without a cytidine deaminase inhibitor, when combined with new sources, new schedules of radiation, and/or new categories of tumors. The agents of the invention also include 4-N-aminomethyl 5-fluoro-2'-deoxycytidine (4-N-aminomethyl FdC), which may be coadministered with a cytidine deaminase inhibitor.

BACKGROUND OF THE INVENTION

In past studies with rodent tumors (1–3), the present inventor found that it was necessary to coadminister N-(phosphonoacetyl)-L-aspartate (PALA) and 5-fluoro-2'-deoxycytidine (FdC) plus tetrahydrouridine ($H_4U$) or 5-fluoro-2'-deoxyuridine (FdU) with 5-chloro-2'-deoxycytidine (Cytochlor, CldC) to achieve clinically relevant radiosensitization. The inventor stated and published (1–3) that the protocol was unamenable to modifications, i.e. it was necessary to coadminister three drugs with Cytochlor for biologically significant radiosensitization to occur. The inventor previously followed this protocol utilizing PALA, FdC, $H_4U$ and CldC in his studies with human tumors in nude mice.

SUMMARY OF THE INVENTION

Surprisingly and unexpectedly, in view of the inventor's intensive experience over an 18 year period with rodent tumors, the inventor discovered that, in an unpredictable manner, clinically relevant and biologically meaningful radiosensitization took place with only Cytochlor (CldC) and one other drug, Tetrahydrouridine ($H_4U$), when human tumors were studied CldC, when administered without a cytidine deaminase inhibitor, can also achieve biologically meaningful radiosensitization of tumors.

In the present invention, CldC can be adminstered at a constant dose during the course of a treatment period (the CldC constant dose scheme), administered with a gradual increase, with time, in dose (the gradual CldC dose escalation scheme), or administered with a high loading dose followed by a lower maintenance dose (the CldC loading scheme).

The following experiment with the CldC gradual dose escalation scheme demonstrates that coadministration of Cytochlor and Tetrahydrouridine provides clinically significant radiosensitization (greater than a 3-to 4-fold dose enhancement without toxicity). Nude mice having a tumor composed of human prostate tumor cells (PC-3) were subjected to an 8-week treatment course in the experiment. CldC and $H_4U$ were co-administered to the mice in weeks 1–4 and 8, with no administration of CldC and $H_4U$ in weeks 5–7 (the bye weeks). In the experiment, a gradual CldC dose escalation scheme was used, in which the dose of CldC was increased 10% each of weeks 2–4 with the same dose of CldC adminstered in week 8 as in week 4, but the dose of $H_4U$ was kept constant in weeks 1–4 and 8. Radiation at a dose of 3.5 Gy was given to the mice in the late afternoon of Wednesday, Thursday and Friday of each week. The total dose of radiation was 52.5 Gy delivered in 15 fractions. The gradual escalation of CldC dose co-administered solely with $H_4U$ resulted in 3/5 cures of an irradiated human prostate tumor (PC-3) in nude mice, whereas 2/6 cures occurred by the Standard Protocol utilizing CldC and all three biomodulators. No cures occurred with drugs alone (0/4), or radiation alone (0/5).

In addition to the gradual CldC dose escalation scheme described above, the CldC loading scheme can be used. In the CldC loading scheme, the treatment initially begins with loading doses of CldC followed by maintenance doses of CldC. Compared with the CldC dose escalation scheme, the CldC loading scheme can achieve even higher frequency of cures. The administration of CldC at relatively high loading doses did not result in an increase in weight loss in the test subjects, so CldC given at loading doses have no side effects. A recent tumor inhibition study utilizing the human prostate tumor PC-3 showed that high loading doses of CldC followed by a lower maintenance dose of CldC, wherein a constant dose of $H_4U$ is co-administered with CldC, resulted in dramatic efficacy which surpasses the efficacy obtained with the CldC dose escalation scheme, in which the CldC dose was increased 10% each week for weeks 2–4 in an 8-week treatment with the same CldC dose used in weeks 4 and 8, wherein the dose of $H_4U$ co-administered with CldC was kept constant.

A toxicity study with coadministrations of CldC and $H_4U$ in mice shows that CldC plus $H_4U$ was not toxic at extremely high doses, well over any plausible therapeutic dose. Intensive studies including histopathology and hematological and biochemical analyses showed no toxicity of CldC plus $H_4U$ in mice. Furthermore, CldC plus $H_4U$ was not toxic to dogs or monkeys. In monkeys and mice, $H_4U$ increased the half life of CldC. This is a very important indicator of the efficacy of CldC plus $H_4U$ in the treatment of diseases, in particular tumors in humans. This finding shows that high loading doses followed by maintenance doses can be used to achieve therapeutic efficacy.

The agents of the invention include (a) CldC plus Tetrahydrouridine ($H_4U$), (b) CldC plus Zebularine (Zb), (4,5,6)

(c) 5-chloro-2'-deoxycytidine (CldC) plus a cytidine deaminase inhibitor other than $H_4U$ and Zb (that is, a new inhibitor of cytidine deaminase), (d) CldC and 4-N-methylamino FdC± a cytidine deaminase inhibitor, or (e) CldC without a cytidine deaminase inhibitor.

The agents of the present invention can be combined with radiation to treat tumors. The agents can also be used with new sources or new schedules of radiation to treat tumors, including new categories of tumors not treatable with prior art methods. Hereinafter, unless otherwise specified, the phrase "A plus B" means either (a) substance A and substance B are administered to a subject at about the same time or (b) substance A and substance B are administered to the subject separately with a short time gap, wherein "a short time gap" could range from about 0.1 minute to about 60 minutes, preferably from about 0.5 minute to about 30 minutes, and more preferably from about 0.5 minute to about 10 minutes. Similarly, unless otherwise specified, the phrase "A±B" means that substance A is administered with or without substance B and, if substance A is administered with substance B, substance A and substance B are administered to the subject either at about the same time, or separately with a short time gap, wherein "a short time gap" is as defined above.

New categories of tumors, especially human tumors, that are examples of the targets for the treatment methods of this invention utilizing (a) CldC plus $H_4U$, (b) CldC plus Zb, (c) CldC plus a cytidine deaminase inhibitor other than $H_4U$ and Zb, (d) CldC and 4-N-methylamino FdC± a cytidine deaminase inhibitor, or (e) CldC without a cytidine deaminase inhibitor include 1) tumors which are not immunogenic because of the hypermethylation of a gene expressing a tumor surface antigen, 2) tumors which arose as a result of the hypermethylation of a tumor suppressor gene, 3) tumors which are metastatic because the gene encoding E-cadherin and other adhesion glycoproteins are hypermethylated, 4) tumors which have progressed because of loss of estrogen receptors due to the hypermethylation of estrogen receptor genes, 5) tumors which have arisen due to the hypermethylation of the gene encoding glutathione-S-transferase, an enzyme which inactivates carcinogenic free radicals, which, in turn gives rise to subclones of the tumor which are more aggressive, metastatic and resistant to therapy, 6) tumors which have arisen due to the silencing of the gene for $O^6$ methylguanine methyltransferase, an enzyme which repairs chemical damage to cellular DNA, 7) tumors which have arisen due to silencing the gene for a tissue inhibitor of metaloproteinase-3, 8) tumors which are unstable due to the inappropriate methylation of cytosine, thereby creating hot spots of mutation resulting in C to T transitions which, in turn, give rise to subclones of the tumor which are more aggressive, metastatic and resistant to therapy, and 9) tumors, which specifically fit into categories 1 to 8 because of the elevation of the enzyme 5-methylcytosine DNA transferase, an enzyme found to be elevated in many human malignant tumors and responsible for the hypermethylation of critical genes, thereby silencing them.

One of the embodiments of the present invention is a method for hypomethylating a gene during radiation therapy by administering a biomodulator, $4NCH_3$ amino 5-fluoro-2'deoxycytidine or 4-N-methylamino FdC, with a new function. 4-N-methylamino FdC is an inhibitor of a novel target enzyme: 5-methylcytosine DNA transferase. The structure of this analog with a novel function is shown below:

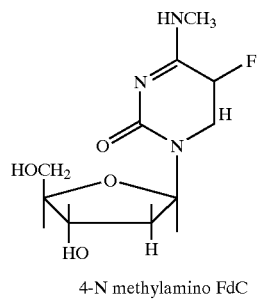

4-N methylamino FdC

This analog (4-N-methylamino FdC) can serve a novel unanticipated function as a tumor directed hypomethlating agent, reactivating genes which are inactivated by hypermethylation of CG dinucleotides in the promoter (controlling) region of the DNA. Although 4-N-methylamino FdC was synthesized along with other derivatives of FdC when FdC was first synthesized at Sloan Kettering in 1961 (7), 4N-methylamino FdC was immediately abandoned as an anti-tumor agent. The major reason for abandoning it was the perception that it was no different from 5-fluorouracil or 5-fluorodeoxyuridine in its mode of action. Obviously, its utility as a hypomethylating agent was now visualized because the observation of hypermethylation of critical genes in tumors is a recent development.

Many human tumors posses high levels of deoxycytidine kinase (dC kinase), an enzyme involved in the salvage of both purines and pyrimidines. Tumors possessing high levels of dC kinase and hypermethylation of critical genes in tumors would be most amenable to this approach utilizing the radiosensitizer CldC± the hypomethylating agent, 4-N-methylamino FdC, ± an inhibitor of cytidine deaminase because the first step in the activation (anabolism) of these analogs is phosphorylation by dC kinase.

4-N-methylamino FdC is a moderate substrate for cytidine deaminase. When administered without an inhibitor of cytidine deaminase, it has the potential to form the tumor directed antimetabolites, 5-fluorouracil, 5-fluoro-2'-dUMP, and 5-fluoro UMP and higher tumor directed DNA and RNA anabolites as well as the hypomethylating agent 4-N-methylamino 5-fluoro-dCTP in a balanced manner so that the array of derivatives will surpass the efficacy of FdC when coadministered with $H_4U$.

More than one half of the tumor suppressor genes known to be involved in inherited forms of human cancer as a result of germ-line mutations are now well characterized to be transcriptionally silenced in association with aberrant promoter region methylation. Included in these human cancers are the tumor suppressor gene controlling retinoblastoma, a lethal cancer affecting children, VHL, a suppressor of human kidney tumors, and p16, a suppressor of a variety of human tumors, including glioblastoma and malignant lymphoma of the brain. These human brain tumors have eluded control by radiation. Hypermethylation associated inactivation of the tumor suppressor p15 INK43 has also been demonstrated in glioblastoma. Human bladder cancer also shows evidence of hypermethylation of the p16 suppressor gene. Indeed, aberrant p16 methylation has been detected in the plasma and serum of liver cancer patients. 60% of individuals with non-small cell lung cancer showed aberrant hypermethylation in at least one of the following genes: p16, the metastatic suppressor gene 'death-associated' protein kinase, the detoxification gene, glutathione-S-transferase, and the DNA repair gene, $O^6$ methyl-guanine DNA methyltransferase.

Normal paired lung tissue showed no aberrancies. 73% of the samples had aberrantly methylated DNA in matched serum samples. MLH-1, when silenced by methylation, results in microsatellite instability in colon, gastric and endometrial cancers. This results in genetic instability of the tumor which leads to tumor progression, metastasis, aggressiveness and resistance to therapy. Of extreme importance to this invention is that this tumor suppressor gene, MLH-1, encodes mismatch repair. When this gene is silenced, the tumor is resistant to treatment with drugs, radiation and radiosensitization. Hypomethylation of this gene by the materials of this invention will enhance radiosensitization by CldC.

BRCA1, a human breast tumor suppressor gene, and the Peutz Jegher suppressor gene are silenced by the elevated activity of 5 methylcytosine DNA transferase in human tumors. The loss of retinoic acid receptor β gene expression in breast tumors and adjacent tissues appear to be due to hypermethylation. Loss of Fhit gene expression is frequent in non-small cell lung cancer in patients who are chronic smokers; hypermethylation appears to be involved. The elevation of 5-methylcytosine DNA transferase activity is an early marker for human lung tumor progression. Inactivation of CACNAIG, a T-type calcium channel gene, is aberrantly methylated at its 5 CpG island in many human tumors. KAI expression is lost by hypermethylation in the progression of human colorectal cancer. The human tumor suppressor gene APC suppresses the formation of multiple adenomatous polyps of the colon and rectum. It has found to be inactivated by methylation in patients whose polyps have progressed to colorectal cancer. Indeed, abnormal regulation of 5-methylcytosine DNA transferase expression occurs during experimental colorectal chemical carcinogenesis in mice. Methylation of the CD44 metastatic suppressor gene occurs in human prostate cancer. Methylation at the CpG island of the endothelium β receptor gene is common in human prostate cancer. In human ovarian cancer, the CPC 3 gene is frequently silenced.

The above summary makes it compelling to consider the merits of a combination of a radiosensitizer, e.g. CldC, with a tumor directed hypomethylating agent, e.g. 4-N-methylamino FdC, as a novel way to control many types of human cancer.

Many childhood and adult tumors, such as hepatoblastoma and rhabdomyosarcoma are due to loss of imprinting. 4-N-methylamino FdC, by virtue of its hypomethylating action has the potential to reverse this loss of imprinting.

Another unexpected advantage of the hypermethylation activity of the agents of this invention is that it allows the intervention of more effective approaches to reactivate silenced tumor suppressor genes. It has been shown that inhibitors of histone deacetylase (such as trichostatin, phenyl butyrate and hexamethylene bisacetamide) are not active in restoring gene expression unless demethylation of gene promoter activity has first occurred. Demethylation by CldC plus a cytidine deaminase inhibitor with 4-N-methylamino FdC±H$_4$U or another cytidine deaminase inhibitor in combination with inhibitors of histone deacetylase opens up new methods of cancer therapy in mammals such as humans in particular.

Within the scope of the present invention is a method of treating a tumor with radiation in which certain genes of the tumor are silenced resulting in the formation of the tumor or resulting in a 1) more aggressive tumor, 2) metastatic tumor, 3) genetically unstable tumor which gives rise to aggressive subclones of the tumor, or 4) tumor resistant to drug or radiation treatment. The activity of CldC or 4-N-methylamino FdC in unsilencing these genes by hypomethylation can thereby restore the activity of genes encoding a) repair enzymes, b) free radical destroying enzymes, c) inhibitors of angiogenesis, d) glycoproteins which prevent tumor cell migration (metastasis), e) cell receptors for hormones or hormone analogs, f) tumor surface antigens whose loss results in the tumor escaping the patient's immune system. In the present invention, a method of hypomethylation of tumor DNA will restore genetic stability by removing hot spots of mutation by inhibiting the target enzyme, 5-methylcytosine DNA transferase.

The present invention includes selective protection of normal tissue, especially in the control of prostate cancer by radiation.

The novel technology of the present invention results in a dramatic enhancement of the radiation dose so that a dose of 70 Gy will be as effective as a dose of 210 or 280 Gy against tumors, in particular human tumors, without damage to underlying normal tissue. Alternatively, the radiation oncologist can provide a much lower dose of radiation such as 23.3 Gy and obtain a tumor kill normally obtained with 70 Gy or 93 Gy (a dangerously high dose), thereby preventing damage to normal tissue.

The present invention presents a novel way of protecting normal tissue when irradiating tumors such as urogenital tumors, including prostate tumors, by administering bisulfite with or without cysteine immediately before the radiation treatment.

BRIEF DESCRIPTIONS OF THE DRAWINGS

Figure 1E:
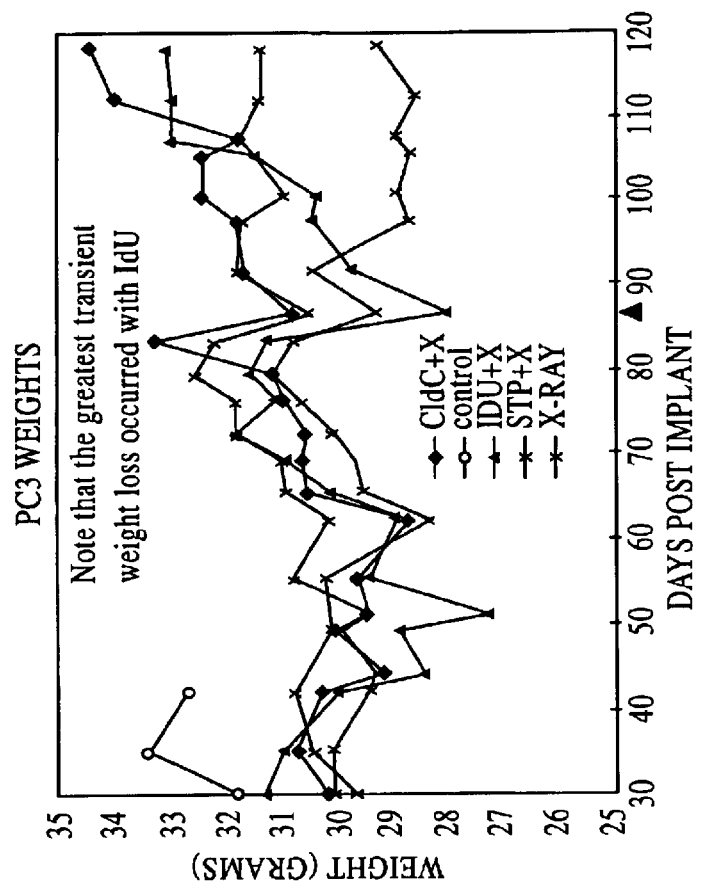
Figure 1D:
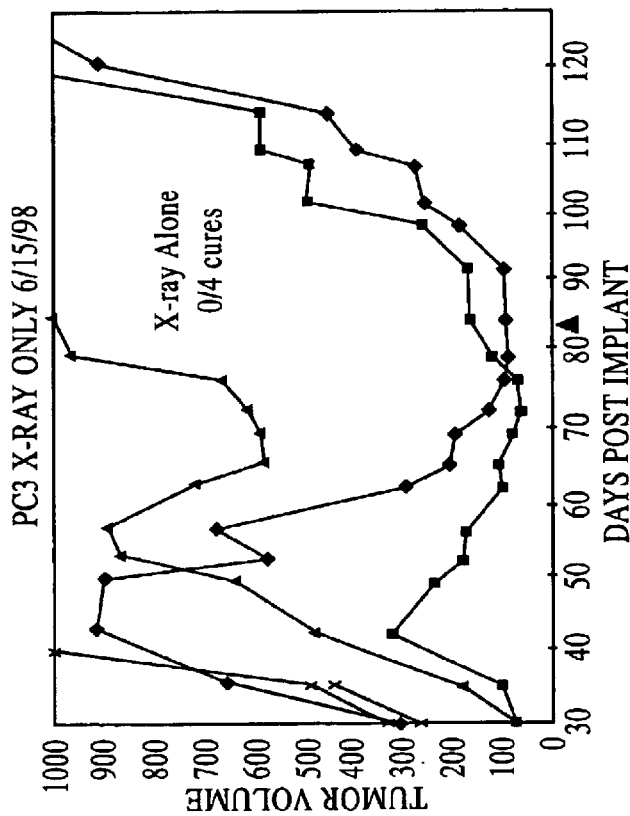

FIGS. 1a–e graphically summarize the data described below in tabular form. FIG. 1a–d present data from tumor inhibition studies, while FIG. 1e presents weight loss data. The solid triangle in FIGS. 1a–e represents the last day of treatment.

1a. The effect of high doses of 5-iodo-2'-deoxyuridine (tested at its maximum tolerated dose).

1b. Results with Standard Protocol with CldC, H4U,FdC and PALA.

1c. Results with escalating doses of CldC with a constant dose of H4U as shown in Table 3.

1d. Results with X-ray alone.

1e. Weight loss and recovery data. Note that the escalating doses of CldC were well tolerated with weight loss no greater than with X-ray alone.

DETAILED DESCRIPTION OF THE INVENTION

I. Simplification of a Complex Protocol

CldC and a single coadministered cytidine deaminase inhibitor, such as Tetrahydrouridine (H$_4$U) or Zebularine (Zb), are surprisingly and unexpectedly sufficient to provide substantial radiosensitization of tumors, including human tumors, whereas, radiosensitization and selectivity and sufficient pool size levels of CldU and incorporation of CldU into tumor DNA was not achieved with several (five) rodent tumors (all of those studied) unless all four drugs (CldC, H$_4$U, FdC and PALA) were administered (Santos 1990; Greer 1990; Greer 1995). Thus, this simplification of the protocol from four drugs to two drugs is unexpected.

The administration of CldC without any cytidine deaminase inhibitor can also provide substantial radiosensitization of tumors, including human tumors. The simplification of the previously standard protocol of using four drugs to one drug is also unexpected.

A study (8) which was based on and followed the inventor's findings and were contracted to expand the inventor's findings with CldC as a radiosensitizer, utilized rodent tumors (a radiation induced fibrosarcoma, RIF-1). The investigators demonstrated that CldC±H$_4$U, at equimolar doses, was far inferior to 5-bromo-2-deoxyuridine (BrdU) as a radiosensitizer. Only when toxic doses of CldC were utilized was there marginal radiosensitization (a dose enhancement ratio of 1.6 with dubious clinical relevance, especially in view of the toxicity encountered). The system utilized in vitro irradiation of mouse tumor cell suspensions after the mice were infused with CldC±H$_4$U or BrdU for 72 hours. In contrast, in studies by the inventor, the tumors are irradiated with fractionated doses while the tumors are growing on the mice—similar to the treatment of human tumors in the clinic.

These results with rodent tumors (8) indicating marginal dose enhancement combined with the complexity of the protocol requiring four drugs to achieve a 3- to 4-fold dose enhancement with rodent tumors resulted in the conclusion by a leading radiation oncologist that the technology utilizing CldC failed to go to clinical trial because of conflicting and marginal results as stated in a publication from the oncologist's laboratory in 1994 (9). The above considerations emphasize the importance of the effectiveness of the newly developed simplification of the protocol in the present invention, demonstrated in the inventor's' recent studies with human tumors in nude mice, rather than with rodent tumors in conventional mice, which now allows the development of the technology to treat human tumors in patients with cancer.

Table 1 shows the general scheme of the schedule of drug administration which was followed in the past with the rodent tumors and with the human tumors prior to the unexpected discovery that two of the modulators. N-(phosphonoacetyl)-L-aspartate (PALA) and 5-fluoro-2'-deoxycytidine (FdC) (+H$_4$U) were dispensable.

The upper table of Table 2 summarizes the results of experiments with the Standard Protocol utilizing CldC, H$_4$U, FdC and PALA against 5 human tumors implanted in nude mice. Included in this table are the results of the experiment in which the protocols were modified. The lower table of Table 2 summarizes the results of an experiment which included the use of escalating doses of CldC plus a constant dose of H$_4$U; PALA and FdC were not coadministered.

Table 3 indicates how the dose of CldC was escalated in weeks I to IV.

The total dose of radiation was 52.5 Gy delivered in 15 3.5 Gy fractions. Tumors were irradiated late in the afternoon of Wednesdays, Thursdays and. Fridays. Note that 3/5 cures occurred with escalating doses of CldC, whereas 2/6 cures occurred with the full protocol. An examination of the weight-loss data indicates that the escalation of the dose of CldC to achieve tumor control does not result in morbidity or side effects. The weight loss is equal to that obtained with radiation alone and is fully recoverable.

CldC, when utilized initially at high doses (loading doses followed by maintenance doses) or when utilized with escalating doses or constant high doses, with or without H$_4$U or Zb or another an inhibitor of cytidine deaminase is an effective radiosensitizer of tumors, especially human tumors. Compared with the standard protocol used in the prior art, the new protocol is simpler, thereby, making the clinical application of CldC more feasible.

Without being bound by the mechanism of action proposed herein, the present inventor believes that the effectiveness of CldC is based, in part, on the expected elevation of dC kinase and dCMP deaminase in tumors, especially human tumors. In contrast to gene therapy, where genes encoding enzymes are delivered to target cells by retroviruses, for example, the present invention is based in part on enzymes which are intrinsically elevated in human tumors; that is, the enzymes are already there. The present invention exploits these enzyme elevations (which are important for the success of the tumor) for a therapeutic advantage. The effectivenss of CldC is also based on the ability of CldC, because of the electronegativity of the Cl atom and its intermediate Van der Waals radius, to have some of the favorable biochemical attributes of FdC on one hand and both BrdUMP and IdUMP and their anabolites on the other. The present inventor notes that a) high doses of CldUMP formed from CldC in tumors will not only overrun the competing levels of TTP but will inhibit its formation because of the affinity of CldUMP for thymidylate synthetase. A single study in Santi's laboratory (10) has shown that the Ki of CldUMP was greater than that of FdUMP but far less than that of BrdUMP and IdUMP (the Ki for the inhibition of thymidylate synthetase by the following substances are: FdUMP=0.015, CldUMP=0.19, BrdUMP=1.4, and IdUMP=1.6). CldUMP, in contrast to BrdUMP and IdUMP, is not dehalogenated by thymidylate synthetase (11). b) Chlorouracil derived from CldC in tumors will invite repair by uracil N-glycosylase (a property of uracil and 5-fluorouracil). When followed by the apurinic/apyrimidinic endonuclease, this should result in additional DNA single strand breaks in tumor cells which should overrun repair and lead to radiosensitization. The accumulation of dUMP due to the inhibition of thymidylate synthetase described in 'a)' above should result in further DNA strand breaks because of the resultant accumulation of uracil in DNA (12). c) CldUTP formed from CldC selectively in tumors will inhibit competing pools of TTP due to inhibition of nucleoside diphosphate reductase (a property of BrdUTP), which is an exquisite inhibitor of that enzyme. The nucleotide pool imbalances caused by this inhibition, in view of studies with other reductase inhibitors, should result in tumor directed apoptosis and strand breaks equivalent to that obtained with 20 Gy (13). d) CldC in DNA will have the capacity to inhibit 5-methylcytosine DNA transferase in an analogous manner by which FdC inhibits this enzyme (14–16). The processive enzyme, 5 methylcytosine DNA methyltransferase, is inhibited via a similar mechanism by which FdUMP inhibits thymidylate synthetase(16). Both enzymes normally encounter a hydrogen in the 5 position instead of an electronegative halogen, which they must extract to replace with a methyl group. Both enzymes are covalently inhibited because they can not extract the electronegative fluorine or chlorine group.

The present inventor wants to emphasize that an important feature of CldUMP formed from CldC is that CldUMP can inhibit thymidylate synthetase (TS), an important source of the normal metabolite TTP (which competes with CldUTP for incorporation into DNA). Therefore, CldC in high concentrations will not only over run the cellular pools of TTP, but will inhibit their formation. This could account for the omission of FdC and PALA in the treatment methods of the present invention without a loss of efficacy of CldC plus H$_4$U. FdC and PALA in the Standard Protocol mainly function by lowering the pools of TTP.

II. New Sources of Radiation

The technology of the present invention is applicable to sources of radiation used in the prior art and also to new sources of radiation.

A. Protons

For deep tumors, the methods of the present invention can utilize protons as a radiation source. In radiation therapy of tumors, protons as a radiation source can be combined with (a) CldC plus $H_4U$, (b) CldC plus Zb, (c) CldC plus a cytidine deaminase inhibitor other than $H_4U$ or Zb, (d) CldC and 4-N-methylamino FdC± a cytidine deaminase inhibitor, or (e) CldC without a cytidine deaminase inhibitor.

Unless otherwise specified, all through the patent application, the phrase "administering CldC and 4-N-methylamino FdC # a cytidine deaminase inhibitor" means that (A) CldC plus a cytidine deaminase inhibitor plus 4-N-methylamino FdC are administered, (B) CldC plus a first cytidine deaminase inhibitor are adminstered separately from 4-N-methylamino FdC± a second cytidine deaminase inhibitor, (C) CldC is administered separately from 4-N-methylamino FdC± a cytidine deaminase inhibitor, or (D) CldC is administered separately from 4-N-methylamino FdC, wherein the first and second cytidine deaminase inhibitors can be the same or different.

B. Brachytherapy

Because of the sensitization by Cytochlor (CldC) to low dose rates of radiation, a radiation source such as yttrium 90 or iridium needles, implanted proximal to a tumor, e.g. prostate or breast tumor, can be combined with (a) CldC plus $H_4U$; (b) CldC plus Zb; (c) CldC plus a cytidine deaminase inhibitor other than $H_4U$ or Zb; (d) CldC and 4-N-methylamino FdC± a cytidine deaminase inhibitor, or (e) CldC without a cytidine deaminase inhibitor in radiation therapy of tumors to achieve remarkable responses, not achievable with external beam radiation.

C. Monoclonal Antibodies Attached to Radionuclides (yttrium 90, for Example).

Because of the sensitization by Cytochlor to low dose rates of radiation, in radiation therapy of tumors, a subject can be given a systemic treatment of (a) CldC and $H_4U$; (b) CldC and Zebularine; (c) CldC plus a cytidine deaminase inhibitor other than $H_4U$ or Zebularine; (d) CldC and 4-N-methylamino FdC± a cytidine deaminase inhibitor, or (e) CldC without a cytidine deaminase inhibitor, wherein the systemic treatment is coupled with administration of monoclonal antibodies attached to a radionuclide to the subject. This adds an entirely new dimension to the technology due to the fact that it allows a treatment of a metastatic disease. The monoclonal antibody will seek out the nests of metastatic foci and eradicate them when they have migrated from the primary site. It is not necessary for the monoclonal antibody (mAb) to be attached to the radionuclide, e.g. yttrium 90, to interact with every cell in the metastatic clone because of the bystander effect; that is, cells proximal to the cell which attracted the mAb will nonetheless be a target for the β emission. The current invention makes the treatment of cancer metastasis feasible.

The two shortcomings of this 'theoretical approach' have been: a) the signal sent out by the tumor cell has been too weak, i.e., most tumors hide their unique surface antigens, b) the target has not been sufficiently sensitive to the 'intelligent' missile'. The current invention addresses those two problems by a) the hypomethylating action of CldC when it is incorporated as such into DNA or of 4-N-methylamino FdC and FdC which leads to the expression of tumor surface antigens which can serve as a signal to selectively attract the mAb conjugated to yttrium 90 and b) by the radiosensitization effect of CldC. The eradication of metastatic disease at unknown sites is a most critical and novel aspect of this invention.

D. The Gamma Knife

The use of multiple sources of radiation all focused on a very small region in a solid tumor, e.g. a brain tumor, is an approach that has improved the outlook for controlling the solid tumor, such as glioblastoma and other brain tumors. However, there is a need for a more effective tumor directed killing. Human tumors of the brain have 125 to 130-fold higher levels of dCMP deaminase than the surrounding brain cortex. dCMP deaminase is the enzyme responsible for converting the prodrug, CldC, to the radiosensitizer, CldUTP.

The combination of CldC and gamma radiation from the gamma knife will provide great potential for cures of solid tumors, especially brain tumors.

A patient can be given, orally or by intravenous infusion, the agents of the present invention, i.e. (a) CldC and $H_4U$; (b) CldC and Zebularine; (c) CldC and a cytidine deaminase inhibitor other than $H_4U$ or Zebularine; (d) CldC and 4-N-methylamino FdC± a cytidine deaminase inhibitor, or (e) CldC without a cytidine deaminase inhibitor, and also given 3 to 4 treatments with the gamma knife. Infusion of the agents via the carotid artery or a vein by a portable pump one week prior to the treatment with the gamma knife and during a week of treatment with the gamma knife would be the method of choice if oral administration is not fruitful.

E. 3-Dimensional Conformal Radiation

By using several different angles rather than one plane of radiation, the damage to normal tissue can be diminished by spreading the radiation to diverse areas of normal tissues. In addition to this 3D approach, the source of radiation can be modified by the use of a multileaf colimator to have the radiation conform to the shape of the tumor, wherein the tumor shape is first determined by computer assisted tomography. The use of the agents of the present invention, i.e. (a) CldC and $H_4U$; (b) CldC and Zebularine; (c) CldC plus a cytidine deaminase inhibitor other than $H_4U$ and Zebularine; (d) CldC and 4-N-methylamino FdC± a cytidine deaminase inhibitor, or (e) CldC without a cytidine deaminase inhibitor, in combination with 3D Conformal Radiation Therapy has the potential to provide tumor cures which would otherwise not be possible. The combination can significant decrease rectal bleeding, incontinence and impotency in the management of prostate cancer, or lessen the extent of prostate tumor progression, metastasis and tumor aggressiveness.

F. Steriotactic Radiosurgery

The agents of the present invention, i.e. (a) CldC and $H_4U$; (b) CldC and Zebularine; (c) CldC plus a cytidine deaminase inhibitor other than $H_4U$ and Zebularine; (d) CldC and 4-N-methylamino FdC± a cytidine deaminase inhibitor, or (e) CldC without a cytidine deaminase inhibitor, can also be combined with steriotactic radiosurgery to increase the efficacy of the radiation therapy. This involves the use of a steriotactic frame and is usually utilized to treat brain tumors. However, steriotactic radiosurgery can be adapted to treat tumors tissues other than the brain.

III. New Methods of Delivery

A. Sustained, slow. Intratumoral Release of CldC and the Modulators.

Polymers such as bis(p-carboxyphenoxy)propane-sebacic-acid and other agents such as lecithin suspensions may be employed to obtain sustained intratumoral release of CldC alone or CldC and a cytidine deaminase inhibitor, e.g. $H_4U$, with or without 4-N-methylamino FdC. Other sustained, slow release formulations known in the art can also be used.

B. Perfusion of the Tumor with CldC alone or CldC and the Modulators.

IV. New Deaminase Inhibitors

Other than tetrahydrouridine ($H_4U$) and Zebularine (1-β-ribofuranocyl-1,2-dihydropyrimidin-2-one), i.e. Zb, the use of other deaminase inhibitors to enhance the efficacy of CldC and/or FdC as a radiosensitizer and modulator is contemplated in the present invention.

Because tetrahydrouridine is unstable in acid, it is not practical to administer tetrahydrouridine orally unless a coated form of the drug is utilized. Oral administration may be possible for the other drugs. Oral administration is the ideal route of administration, of course. Because CldC, FdC and 4-N-methylamino FdC are prodrugs, CldC, FdC and 4-N-methylamino FdC can be administered orally, wherein the enteric route is a desirable route of administration.

Cytidine deaminase inhibitors other than tetrahydrouridine and Zebularine can include the following.

A. Pyrimidin-2-one nucleosides, such as 5-F pyrimidin-2-one-nucleosides (4, 5, 6), other than 1-β-ribofuranocyl-1,2-dihydropyrimidin-2-one.

B. F pyrimidin-2-one nucleosides.

C. Diazepin-2-1-nucleosides.

Diazepin-2-1-nucleosides act in an analogous manner to adenosine deaminase inhibitors, which are potent inhibitors. Diazepin-2-1-nucleosides are acid labile but very potent, being 10 times more potent than tetrahydrouridine. Diazepin-2-1-nucleosides result in greater efficacy of CldC and/or FdC as a radiosensitizer and a modulator, respectively.

D. 1-(2-Deoxy-2-fluoro-β-D arabinofuranosyl)-1,2-dihydropyrimidin-2-one.

E. 2'-Deoxy-2'-F-arazebularine.

F. Diazoepinone.

G. 4-Hydromethyl-2-oxopyrimidin-2-one nucleoside.

H. 2'-Fluoro-2'-deoxyarabinosyl-tetrahydrouracil, which is unlikely to undergo N-glycosidic cleavage.

V. The present invention is most effective against human tumors possessing high levels of 5-methylcytosine DNA transferase. A high level of 5-methylcytosine DNA transferase is a characteristic of many tumors.

5-Methylcytosine DNA transferase is a novel target enzyme inhibited by (a) FdC plus $H_4U$, (b) 4-N-methylamino FdC with or without an inhibitor, e.g. $H_4U$ or Zb, of cytidine deaminase, or (c) CldC with or without an inhibitor, e.g. $H_4U$ or Zb, of cytidine deaminase. 5-Methylcytosine DNA transferase is a mutagenic cancer-causing enzyme responsible for metastasis, tumor progression and resistance to therapy (17,18).

5-Methylcytosine DNA transferase may be responsible for the origin of the tumor. The chlorinated and fluorinated pyrimidine analogs inhibit this processive enzyme irreversibly and non-stoichiometrically. The enzyme is inhibited only in the presence of S-adenosyl methione. The mechanism of inhibition is as follows: the enzyme usually extracts an H from the 5 position of cytosine in DNA and adds a methyl group from S-adenosyl methionine. When CldC, FdC or 4-N-methylamino FdC is in DNA, the enzyme cannot extract the electronegative chlorine or fluorine and is stuck and idles in that position. The processive enzyme cannot traverse the DNA and interferes with transcription and fails to methylate the downstream CG dinucleotides in the daughter strand opposite $G^{me}C$ in the parental strand.

The agents of the present invention, i.e. (a) CldC+$H_4U$; (b) CldC+Zb; (c) CldC plus a cytidine deaminase inhibitor other than $H_4U$ or Zb; (d) CldC and 4-N-methylamino FdC± a cytidine deaminase inhibitor, or (e) CldC without a cytidine deaminase inhibitor will result in tumor-directed hypomethylation. In the past, FdC+$H_4U$ were added to lower the competing pools of TTP which interfere with the incorporation of CldUTP into tumor DNA. 4-N-methylamino FdC when coadministered with a cytidine deaminase inhibitor will not lower TTP pools, it will serve, instead, solely as a tumor-directed hypomethylating agent. CldC at high doses will act like FdC as a hypomethylating agent and at the same time it will act as a radiosensitizer and inhibit the reductase (like BrdU and IdU) and inhibit thymidylate synthetase, a target enzyme in cancer chemotherapy (like FdU or 5-fluorouracil).

What is surprising and unexpected with the present invention is that CldC is a multifaceted drug, like 5-bromo-2'-deoxyuridine or 5-iodo-2'-deoxyuridine in some ways, and like 5-fluoro-2'-deoxyuridine or FdC in other ways.

VI. One of the aspects of the present invention utilizes a nucleoside analog, 4-N-methylamino 5-fluoro-2'deoxycytidine (4-N-methylamino FdC), with a novel, unanticipated function.

The structure of the novel drug, 4-N-methylamino FdC, is shown above. 4-N-methylamino FdC does not absolutely require the coadministration of an inhibitor of cytidine deaminase. It is only a moderate substrate of cytidine deaminase. When co-administered with $H_4U$, 4-N-methylamino FdC will act only as a hypomethylating agent without generating FdUMP, FUMP. FUra, FdU or FUTP or FdUTP. It will not interfere with RNA processing and will not generate inhibitors of thymidylate synthetase as is the case with 5-fluorouracil (FUra), 5-fluoro-deoxyuridine (FdU) or 5-fluorodeoxycytidine (FdC).

VII. The agents of the present invention, e.g. (a) CldC plus $H_4U$, (b) CldC plus Zebularine, (c) CldC plus a cytidine deaminase inhibitor other than $H_4U$ or Zb, (d) CldC and 4N-methylamino FdC± a cytidine deaminase inhibitor, or (e) CldC without a cytidine deaminase inhibitor, when combined with radiation, are especially effective against tumors, such as human tumors, which are not immunogenic because they do not express tumor surface antigens, e.g. HLA. The present invention is especially effective against tumors which mask tumor surface or HLA antigens, i.e. non-immunogenic tumors.

These non-immunogenic tumors silence antigen forming genes by hypemethylation. The agents of the present invention, i.e. (a) CldC plus $H_4U$, (b) CldC plus Zebularine, (c) CldC plus a cytidine deaminase inhibitor other than $H_4U$ or Zb, (d) CldC and 4-N-methylamino FdC± a cytidine deaminase inhibitor, or (e) CldC without a cytidine deaminase inhibitor, result in the expression of tumor surface (HLA) antigens. This allows the patient to mount an immune response against the tumor and assures the effectiveness of the use of monoclonal antibodies attached to radionuclides versus the metastatic foci of the tumor. The agents of the present invention have a remarkable effect against tumors which 'hide' their unique antigens (and many successful tumors do hide their antigens) so that greater efficacy will be obtained. This is consistent with the goal of radiotherapy which is to bring the tumor burden down so that the patient's immune system can control the remaining surviving cells.

VIII. The agents of the present invention, e.g. (a) CldC plus $H_4U$, (b) CldC plus Zebularine, (c) CldC plus a cytidine deaminase inhibitor other than $H_4U$ or Zb, (d) CldC and 4N-methylamino FdC± a cytidine deaminase inhibitor, or (e) CldC without a cytidine deaminase inhibitor, when combined with radiation are especially effective against tumors, e.g. human tumors, which arise as a result of the inactivation of a tumor suppressor gene.

The agents of the present invention are especially effective against tumors which have arisen as a result of the silencing (hypermethylation) of tumor suppressor genes. Because many tumors arise as a result of the inactivation of a tumor suppressor gene—not by mutation or deletion but by methylation, which results in gene silencing, the agents of the present invention, i.e. (a) CldC plus H$_4$U, (b) CldC plus Zebularine, (c) CldC plus a cytidine deaminase inhibitor other than H$_4$U or Zb, (d) CldC and 4-N-methylamino FdC± a cytidine deaminase inhibitor, or (e) CldC without a cytidine deaminase inhibitor, play a role in re-expression of the inactive tumor suppressor gene which will then result in tumor cures.

IX. The agents of the present invention, e.g. (a) CldC plus H$_4$U, (b) CldC plus Zebularine, (c) CldC plus a cytidine deaminase inhibitor other than H$_4$U or Zb, (d) CldC and 4N-methylamino FdC± a cytidine deaminase inhibitor, or (e) CldC without a cytidine deaminase inhibitor, when combined with radiation are especially effective against cadherin tumors which give rise to metastatic subclones because of the silencing of the cadherin gene. This occurs often in breast and prostate tumors and squamous cell carcinoma of the lung, for example.

Human tumors often become metastatic as a result of the inactivation of the gene encoding cadherin, a sticky glycoprotein which prevents cells from migrating to distant sites. This gene is often inactivated not by mutation or deletion but by methylation which results in gene silencing. Most metastatic breast tumors are cadherin$^-$, i.e. lacking the expression of the cad gene.

X. The agents of the present invention, e.g. (a) CldC plus H$_4$U, (b) CldC plus Zebularine, (c) CldC plus a cytidine deaminase inhibitor other than H$_4$U or Zb, (d) CldC and 4N-methylamino FdC± a cytidine deaminase inhibitor, or (e) CldC without a cytidine deaminase inhibitor, when combined with radiation are especially effective against tumors which can not be treated with estrogen and androgen analogs because the hormone receptors are absent.

Human breast and prostate tumors can be controlled by hormone analogs when their hormone receptors are intact. For example, approximately 40% of breast tumors are estrogen receptor (ER) negative and, therefore, can not be treated with tamoxifen. It has been shown that in the vast majority of cases that the ER gene is inactivated not by mutation or deletion but by methylation of cytosine.

XI. The agents of the present invention, e.g. (a) CldC plus H$_4$U, (b) CldC plus Zebularine, (c) CldC plus a cytidine deaminase inhibitor other than H$_4$U or Zb, (d) CldC and 4N-methylamino FdC± a cytidine deaminase inhibitor, or (e) CldC without a cytidine deaminase inhibitor, when combined with radiation are especially effective against tumors which have low levels of glutathione-S-transferase. Glutathione-S-transferase is an antioxidant enzyme and its silencing may have given rise to the tumors. Its silencing may lead to subclones of the tumor which more aggressive, metastatic, and resistant to therapy.

XII. The agents of the present invention, e.g. (a) CldC plus H$_4$U, (b) CldC plus Zebularine, (c) CldC plus a cytidine deaminase inhibitor other than H$_4$U or Zb, (d) CldC and 4N-methylamino FdC± a cytidine deaminase inhibitor, or (e) CldC without a cytidine deaminase inhibitor, when combined with radiation are especially effective against tumors which have low levels of O$^6$ methyl guanine methyltransferase. O$^6$ methyl guanine methyltransferase is a repair enzyme which repairs alkylated purines. Its silencing may lead to subclones of the tumor which are more aggressive, resistant to therapy and metastasis.

XIII. The agents of the present invention, e.g. (a) CldC plus H$_4$U, (b) CldC plus Zebularine, (c) CldC plus a cytidine deaminase inhibitor other than H$_4$U or Zb, (d) CldC and 4N-methylamino FdC± a cytidine deaminase inhibitor, or (e) CldC without a cytidine deaminase inhibitor, when combined with radiation are especially effective against tumors which have low levels of the tissue inhibitor of metalloproteinase-3. The tissue inhibitor of metalloproteinase-3 (TIMP-3) can suppress tumor growth, angiogenesis, invasion and metastasis in many human tumors.

XIV. The agents of the present invention, e.g. (a) CldC plus H$_4$U, (b) CldC plus Zebularine, (c) CldC plus a cytidine deaminase inhibitor other than H$_4$U or Zb, (d) CldC and 4N-methylamino FdC± a cytidine deaminase inhibitor, or (e) CldC without a cytidine deaminase inhibitor, combined with radiation are especially effective against tumors which have arisen because of mutation in the p53 tumor suppressor gene. The analogs change an unstable human tumor into a more genetically stable one.

Many human tumors are genetically unstable and give rise to more metastatic, more aggressive subclones that may also be resistant to therapy. The reason for this is that the inappropriate methylation of cytosine by 5-methylcytosine DNA transferase has occurred. When $^{me}$C is deaminated either spontaneously or by the tumorigenic enzyme 5-methylcytosine DNA transferase, it results in mutation (a C to T transition). Tumors such as those in the prostate gland progress to greater tumorigenesis by accumulating mutations in the p53 tumor suppressor gene. With the tumor suppressor gene, p53, C to T transitions occur very often in human tumors of the lung (46%), colon (79%), bladder (47%) ovary (36%), brain (75%) and breast (40%). These transitions are due to the action of 5-methylcytosine DNA transferase which not only methylates C at CG dinucleotides, but also deaminates $^{me}$CG to form TG base pairs and moreover, prevents the mismatch repair enzyme from repairing TG mismatches (TA and CG are normal base pair matches). 5-Methylcytosine DNA transferase also, remarkably, methylates uracil in DNA which is generated either by spontaneous deamination of cytosine or by the action of 5-methylcytosine DNA transferase (17). This forms a TG base pair and thus indirectly prevents the removal of uracil from DNA, which would normally be removed from DNA by a repair cascade beginning with uracil N-glycosidase. 5-Methylcytosine DNA transferase also directly inhibits uracil N-glycosidase.

Thus, the methyl transferase is a mutagenic and tumorogenic enzyme (18) which is elevated in many human tumors (19, 20). 5-Methylcytosine DNA transferase is the target of the deoxycytidine analogs of this invention. Therefore, the action of the deoxycytidine analogs on 5-methylcytosine DNA transferase in combination with radiosensitization makes the method of using CldC in the present invention a powerful approach to control human cancer. The inactivation of p53 is most important in view of the fact that tumors and tumor cell lines lacking p53 are resistant to radiation.

$^{me}$C is a 'hot-spot' of mutation and the agents of the present invention, i.e. (a) CldC plus H$_4$U, (b) CldC plus Zebularine, (c) CldC plus a cytidine deaminase inhibitor other than H$_4$U or Zb, (d) CldC and 4-N-methylamino FdC± a cytidine deaminase inhibitor, or (e) CldC without a cytidine deaminase inhibitor, can remove these hot spots by virtue of hypomethylation.

Items VII—IX have as their basis the elevation of 5-methylcytosine DNA transferase in human tumors and the ability of the agents of the present invention, i.e. (a) CldC plus H$_4$U, (b) CldC plus Zebularine, (c) CldC plus a cytidine deaminase inhibitor other than H$_4$U or Zb, (d) CldC and 4-N-methylamino FdC± a cytidine deaminase inhibitor, or (e) CldC without a cytidine deaminase inhibitor, to hypomethylate genes which have been silenced by hypermethylation.

CldC has the advantage of being both a radiosensitizer and a hypomethylating agent. 4N-methylamino FdC is not a radiosensitizer, but when coadministered with H$_4$U or another cytidine deaminase inhibitor, it is a more potent hypomethylating agent. When 4-N-methylamino FdC is administered without a cytidine deaminase inhibitor, 4-N-methylamino FdC is still not a radiosensitizer, 4-N-methylamino FdC, however, remains as a hypomethylating agent, but it also generates an array of antimetabolites that inhibit tumor enzymes involved in DNA and RNA metabolism.

The importance and novelty of this approach is that it more reasonably assures a tumor cure without damage to underlying tissue. Instead of using a high dose of radiation, which could affect normal tissue (in spite of the great selectivity of the radiosensitizer of this invention), the present invention involves an independent strategy or approach vs the remaining cells of the tumor which may have escaped the lethal effects of radiation. CldC itself and the nucleoside analogs make CldC a more effective radiosensitizer because they may have the dual role of affecting gene expression in surviving tumor cells by virtue of its inhibition of 5-methylcytosine DNA transferase. This will more effectively assure complete tumor control, or at least prevent tumor progression and metastasis, by A) restoring the tumor cells to a normal state by reactivating tumor suppressor genes and B) restoring genetic stability to the surviving cells by 1) reactivating the transcription of mRNA encoded genes whose protein products prevent further DNA modification (additional alterations in DNA could lead to further progression towards neoplasia, 2) reactivating the expression of enzymes which repair alterations in the DNA of the surviving cells, or, more directly, 3) preventing the epigenetic inheritance, via maintenance methylation, of hot spots of mutation in the DNA of the surviving cells.

XV. The present invention allows a method of treatment in which the tumor is irradiated prior to drug treatment to induce greater deoxycytidine kinase (dCK) activity in the target cells. Deoxycytidine kinase initially converts CldC, FdC and 4-N-methylamino FdC to their anabolites, CldCMP, FdCMP, and 4-N-methylamino FdCMP, respectively.

Radiation also activates thymidine kinase (TK) which increases the conversion of CldU and FdU derived from CldC and FdC into higher metabolites.

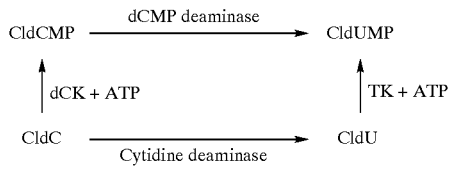

XVI. In the case of human prostate cancer, the technology utilizes a slow release suppository of a low dose of bisulfite to protect the rectum by inactivating 5-CldC and converting it to deoxyuridine (a safe normal metabolite and an antagonist of toxicity and radiosensitization). This will protect the rectum from the effects of radiation without diminishing the radiosensitivity of the prostate tumor. Bisulfate deaminates and dehalogenates CldC as a precursor to DNA and will dehalogenate CldU when it is incorporated into the DNA of rectal tissue. Surrounding non-tumor genital tissue can also be protected by controlled localized administration of bisulfite, a free radical scavenger.

The patient would be given a slow release rectal suppository of a low safe dose of bisulfite with or without cysteine (also a free radical scavenger) 1 hr prior to irradiation of his prostate tumor. The patient will be first tested for bisulfite sensitivity. This course of treatment will not be given to asthmatics or to patients having sulfite oxidase deficiency. Bisulfite sensitivity is extremely rare.

The agents of the present invention include (a) CldC plus H$_4$U, (b) CldC plus Zebularine, (c) CldC plus a cytidine deaminase inhibitor other than H$_4$U or Zb, (d) CldC and 4-N-methylamino FdC± a cytidine deaminase inhibitor, or (e) CldC without a cytidine deaminase inhibitor. Other than H$_4$U or Zb, 2'-deoxytetrahydrouridine (dH$_4$U) can also be used as the cytidine deaminase inhibitor.

Some aspects of the invention take advantage of three properties of CldC in being a (1) radiosensitizer, (2) hypomethylating agent, and (3) an indirect inhibitor of the formation of a competing metabolite. By utilizing these three properties of CldC, the present invention simplifies the clinical treatment regiments known in the prior art. For instance, the agents of the present invention can be administered to the subject without the administration of an inhibitor for the formation of an metabolite, i.e. TTP, that competes with the incorporation of a radiosensitizing metabolite, i.e. CldUTP, of CldC into DNA, wherein such inhibitors can be 5-fluoro-2'-deoxycytidine (FdC), 5-fluoro-2'-deoxyuridine (FdU) or N-(phosphonacetyl)-L-aspartate (PALA).

The agents of the present invention are effective in treating tumors, preferably solid tumors. The tumors that can be treated with the agents of the present invention include tumors of the breast, lung, brain, liver, kidney, ovary, uterus, testis, pancreas, gastrointestinal tract, head and neck, nasopharynx, skin, and prostate, and orofacial tumors.

In the present invention, CldC can be administered to a subject in need thereof at a dose of about 5 mg per kg body weight per day to about 10g per kg body weight per day. The preferred dose is about 50 mg per kg body weight per day to about 6 g per kg body weight per day. The other agents, i.e. H$_4$U, Zebularine, cytidine deaminase inhibitors other than H$_4$U or Zebularine, and 4-N-methylamino FdC, of the present invention can be administered to the subject at a dose ranging from about 1/50th to about ½ preferably about 1/30th to about 1/10th, the dose of CldC.

The agents of the present invention can be administered either at about the same dose throughout a treatment period, in an escalating dose regiment, or in a loading-dose regiment, in which a loading dose is about 2 to 5 times a maintenance dose. Alternatively, the dose for the agents of the present invention can be varied during the course of a treatment period according to the condition of the subject being treated and/or the severity of the disease being treated as judged to be appropriate by one skilled in the art.

The agents of the present invention can be administered one to four times a day. The treatment with the agents of the present invention can be repeated daily or temporarily stopped for up to several days during the course of the treatment of the tumor. The irradiation can begin after the first administration of CldC. Alternatively, the irradiation can begin after an interval of about 4 hours to about 18 hours, preferably about 6 to 14 hours, after the last administration of CldC.

The radiation dose can be the same or ¼ to ¾ the dose given to patients not receiving the agents of the present invention.

The doses of the agents of the present invention and the interval between administrations, as well as the frequency of administration, can be determined by one skilled in the art based on the condition of the patient and the severity of the disease to be treated. The interval between drug therapy and radiation treatment may also be varied.

The agents of the present invention can be administered parenterally or enterally. However, for tetrahydrouridine to be administered orally, it must be in a formulation which protects it from acids. The parenteral routes include intravenous, subcutaneous, intramuscular or intraperitoneal injection, intravenous or intraarterial infusion, or dermal administration. Also within the scope of the present invention are methods of treating tumors or protecting normal tissue during radiotherapy of tumors by administering the agents of the present invention via slow release formulations prepared according to methods known in the art.

The agents of the present invention can be administered with or without a pharmaceutically acceptable carrier in a pharmaceutical composition. Included within the scope of the present invention is a pharmaceutical composition comprising CldC and 4-N-methylamino FdC, with or without a pharmaceutically acceptable carrier or excipient.

The subjects that can be treated by the agents of the present invention or the methods of the present invention include animals, such as mammals, and preferably humans.

The agents of the present invention can be obtained commercially or prepared from intermediates which are commercially available by one skilled in the art. The processes of preparation of most of the agents of the present invention are disclosed in U.S. Pat. Nos. 4,894,364 and 5,985,266, the disclosures of which are hereby incorporated by reference.

Other references which may be of interest are also listed below (21–69).

REFERENCES

1. Santos, O, Perez, L, Briggle, T, Boothman, D, Greer, S. 1990. Radiation, pool size and incorporation studies in mice with 5-chloro-2'-deoxycytidine. *Int. J. Radiat. Oncol. Biol. Phys.* 19:357–365.
2. Greer, S, Santos, O, Gottlieb, C, Schwade, J., Marion, S. 1990. 5-Chlorodeoxycytidine, a radiosensitizer effective against RIF-1 and Lewis lung carcinoma, is also effective against a DMBA-induced mammary adenocarcinoma and the EMT-6 tumor in BALB/c mice. *Int. J. Rad. Oncol. Biol. Phys.* 22:505–510.
3. Greer, S, Schwade, J, Marion, S. 1995. Five-chlorodeoxycytidine and biomodulators of its metabolism result in fifty to eighty percent cures of advanced EMT-6 tumors when used with fractionated radiation. *Int. J. Rad. Oncol. Biol. Phys.* 32:1059–1069.
4. Kim, C-H., Marquez, V., Mao, D., Haines, D., McCormack, J. 1986. Synthesis of pyrimidin-2-one nucleoside as acid-stable inhibitors of cytidine deaminase. *J. Med. Chem* 29:1374–1380.
5. Marquez, V. 1994. Inhibition of cytidine deaminase: mechanism and effects of the metabolism of antitumor agents. In: *Developments in Cancer Chemotherapy*, Robert I. Glazer, ed, CRC Press, Boca Raton, Fla., pp. 92–114.
6. Kelly, J., Driscoll, J., McCormack, J., Roth, J., Marquez, V. 1986. Furanose-pyranose: isomerization of reduced pyrimidine and cyclic urea ribosides. *J. Med. Chem.* 29: 2351–2358.
7. Wempen, I., Duschinsky, R., Kaplan, L., and Fox, J. 1961. Organic and biological chemistry. Thiation of Nucleosides. IV. The synthesis of 5-fluoro-2'-deoxycytidine and related compounds. *J. Amer. Chem. Soc.* 83:4755–4766.
8. Russell, K., Rice, G., Brown, J. 1986. In vivo and in vitro radiation sensitization by the halogenated pyrimidine 5-chloro-2'-deoxycytidine. *Cancer Res.* 46:2883–2887.
9. Kinsella, T., Kunugi, K., Vielhuber, K., McCulloch, W., Liu, S-H., and Cheng, Y-C. 1994. An in vivo comparison of oral 5-Iodo-2'-deoxyuridine and 5-iodo-2-pyrimidinone-2'doexyribose toxicity, pharmacokinetics, and DNA incorporation in athymic mouse tissues and the human colon cancer xenograft, HCT-116. *Cancer Res.* 54:2695–2700.
10. Wataya, Y., Santi, D., Hansch, C. 1977. Inhibition of *Lactobacillus casei* thymidylate synthetase by 5-substituted 2'-deoxyuridylates. Preliminary quantitative structure-activity relationship. *J. Med. Chem.* 20: 1469–1473. In: Balzarini, J., DeClerq, E., Mertes, M., Shugar, D., Torrence, P. 1982. 5-Substituted 2'-deoxyuridines: Correlation between inhibition of tumor cell growth and inhibition of thymidine kinase and thymidylate synthetase. *Biochem. Pharmacol.* 31:3673–3682.
11. Wataya, Y., Santi, D. 1975. Thymidylate synthetase catalyzed dehalogenation of 5-bromo- and 5-iodo-2'-deoxyuridylate. *Biochem. Biophys. Res. Commun.* 67: 818–823.
12. Caradonna, S, Cheng, Y-C. 1980. The role of deoxyuridine triphosphate nucleotidohydrolase, uracil-DNA glycosylase, and DNA polymerase $\alpha$ in the metabolism of FUdr in human tumor cells. *Mol Pharmacol.* 18:513–520.
13. Hirota, Y, Yoshioka, A, Tanaka, S, et al. 1989. DNA double-strand breaks, and cell death caused by 2-chlorodeoxyadenosine in mouse FM3A cells. *Cancer Res.* 49:915–919.
14. Jones, P, Taylor, S. 1980. Cellular differentiation, cytidine analogs, and DNA methylation. *Cell.* 20:85–93.
15. Kaysen, J, Spriggs, D, Kufe, D. 1986. Incorporation of 5-fluorodeoxycytidine and metabolites into nucleic acids of human MCF-7 breast carcinoma cells. *Cancer Res.* 46: 4534–4538.
16. Osterman, D., DePillis, G., Wu, J. Matsuda, A., Santi, D.1988. 5-Fluorocytosine in DNA is a mechanism-based inhibitor of HhaI methylase. *Biochemistry.* 27:5204–5210.
17; Yang, A,. Shen, J-C, Zingg, J-M, Jones P. 1995. HhaI and HpaII DNA methyltransferase bind DNA mismatches, methylate uracil and block DNA repair. *Nucl. Acids Res.* 23:1380–1387.
18. Jones, P, Rideout, W.,III, Shen, J-C, et al. 1992. Methylation, mutation and cancer. *BioEssays.* 4:33–36.
19. El-Deiry, W., Nelkin, B., Celano, P., Yen, C., Falco, J., Hamilton, S., Baylin, S. 1991. High expression of the DNA methyltransferase gene characterizes human neoplastic cells and progression stages of colon cancer. *Proc. Natl. Acad. Sci. USA.* 88: 3470–3474.
20. Baylin, S. and Herman, J. 2000. Promoter hypermethylation and gene silencing in cancer. *Advances in Gene Tech: DNA, RNA and Cancer*. Miami Nature Biotechnology Winter Symposium, p. 43.
21. Driscoll, J., Marquez, V., Plowman, J., Liu, P., Kelley, J., Barchi, J., Jr. 1991. Antitumor properties of 2(1H)-pyrimidinone rinboside (Zebularine) and its fluorinated analogues. *J. Med. Chem.* 34:3280–3284.
22. Laird, P., Jaenisch, R. 1994. DNA methylation and cancer. *Human Molecular Genetics.* 3: 1487–1495.
23. Doiron, A., Yapp, D., Olivares, M., Zhu, J., and Lehnert, S. 1999. Tumor radiosensitization by sustained intratumoral release of bromodeoxyuridine. *Cancer Res.* 59:3677–3681.
24. Oka, H., Shiozaki, H., Kobayashi, K., Inoue, M., Tahara, H., Kobayashi, T., Takatsuka, Y., Matsuyoshi, N., Hirano, S., Takeichi, M., Mori, T. 1993. Expression of E-cadherin cell adhesion molecules in human breast cancer tissues and its relationship to metastasis. Cancer Res. 53: 1696-1701.

25. Graff, J., Herman, J., Lapidus, R., Chopra, H., Xu, R., Jarrard, D., Isaacs, W., Pitha, P., Davidson, N., Baylin, S. 1995. E-cadherin expression is silenced by DNA hypermethylation in human breast and prostate carcinomas. *Cancer Res.* 55: 5195–5199.
26. Kanai, Y., Ushijima, S., Hui, A., Ochiai, A., Tsuda, H., Sakamoto, M., Hirohashi, S. 1997. The E-cadherin gene is silenced by CpG methylation in human hepatocellular carcinoma. *Int. J. Cancer.* 71: 355–359.
27. Graff, J., Greenberg, V., Herman, J., W., Boghaert, E., Ain, K., Saji, M., Zeiger, M., Zimmer, S., Baylin, S. 1998. Distinct patterns of E-cadherin CpG island methylation in papillary, follicular, hurthle's cell, and poorly differentiated human thyroid carcinoma. *Can. Res.* 58: 2063–2066.
28. Qian, X. and Brent, T. 1997. Methylation hot spots in the 5' flanking region denote silencing of the $O^6$-methylguanine-DNA methyltransferase gene. *Cancer Res* 57:3672–3677.
29. Esteller, M., Hamilton, S., Burger, P., Baylin, S., and Herman, J. 1999. Inactivation of the DNA repair gene $0^6$-methylguanine-DNA methyltransferase by promoter hypermethylation is a common event in primary human neoplasia. *Cancer Res.* 59: 793–797.
30. Lee, W., Morton, R., Epstein, J., Brooks, J., Campbell, P., Bova, G., Hsieh, W., Isaacs, W., Nelson, W. 1994. Cytidine methylation of regulatory sequences near the pi-class glutathione S-transferase gene accompanies human prostatic carcinogenesis. *Proc. Natl. Acad. Sci. USA.* 91: 11733–11737.
31. Esteller, M., Corn, P., Urena, J., Gabrielson, E., Baylin, S., and Herman, J. 1998. Inactivation of glutathione S-transferase P1 gene by promoter hypermethylation in human neoplasia. *Cancer Res.* 58:4515–4518.
32. Bachman, K., Herman, J., Corn, P., Merlo, A., Costello, J., Cavenee, W., Baylin, S., and Graff, J. 1999. Methylation-associated silencing of the tissue inhibitor of metalloproteinase-3 gene suggests a suppressor role in kidney, brain, and other human cancers. *Cancer Res,* 59:798–802.
33. Ferguson, A., Lapidus, R., Baylin; S., Davidson, N. 1995. Demethylation of the estrogen receptor gene in estrogen receptor-negative breast cancer cells can reactivate estrogen receptor gene expression. *Cancer Res.* 55: 2279–2283.
34. Zhau, H., Chang, S., Chen, B., Wang, Y., Zhang, H., Kao, C., Sang, Q., Pathak, S., Chung, L. 1996. Androgen-repressed phenotype in human prostate cancer. *Proc. Natl. Acad. Sci. USA.* 93: 15151–15157.
35. Jarrard, D., Kinoshita, H., Yan, S., Sandefur, C., Hoff, D., Meisner, L., Chang, C., Herman, J., Isaacs, W., Nassif, N. 1998. Methylation of the androgen receptor promoter CpG island is associated with loss of androgen receptor expression in prostate cancer cells. *Can. Res.* 58: 5310–5314.
36. Rideout, W., III, Coetzee, G., Jones, P. 1990. 5-Methylcytosine as an endogenous mutation in the human LDL receptor and p53 genes. *Science.* 249: 1288–1290.
37. Hollstein, M., Sidransky, D., Vogelstein, B., Harris, C. 1991. p53 mutations in human cancers. *Science.* 253: 49–50.
38. Chi, S., deVere White, R., Meyers, F., Siders, D., Lee, F., Gumerlock, P. 1994. p53 in prostate cancer: frequent expressed transition mutations. *J. Natl. Cancer Institute.* 86: 926–933.
39. Merlo, A., Herman, J., Mao, L., Lee, D., Gabrielson, E., Burger, P., Baylin, S., Sidransky, D. 1995. CpG island methylation is associated with transcriptional silencing of the tumor suppressor p16VFKN2/TS1 in human cancers. *Nature Med.* 1: 686–692.
40. Costello, J., Berger, M., Huang, H-J., and Cavenee, W. 1996. Silencing of p16/CDKN2 expression in human gliomas by methylation and chromatin condensation. *Cancer Res.* 56:2405–2410.
41. Zhang, S.-J., Endo, S., Ichikawa, T., Washiyama, K., and Kumanishi; T. 1998. Frequent deletion and 5'CpG island methylation of the p16 gene in primary malignant lymphoma of the brain. *Cancer Res.* 58:1231–1237.
42. Gonzalgo, M., Hayashida, T., Bender, C., Pao, M., Tsai, Y., Gonzales, F., Nguyen, H., Nguyen, T., and Jones, P. 1998. The role of DNA methylation in expression of the p19/p16 locus in human bladder cancer cell lines. *Cancer Res.* 58:1245–1252.
43. Wong, I., Lo. Y., Zhang, J., Liew, C-T., Ng, M., Wong, N., Lai, P., Lau, W., Hjelm, N., and Johnson, P. 1999. Detection of aberrant p16 methylation in the plasma and serum of liver cancer patients. *Cancer Res.* 59: 71–73.
44. Herman, J., Jen, J., Merlo, A., and Baylin, S. 1996. Hypermethylation-associated inactivation indicates a tumor suppressor role for p15$^{INK4B1}$. *Cancer Res.* 56:722–727.
45. Sakai, T., Toguchida, J., Ohtani, N., Yandell, D. W., Rapaport, J. M., Dryja, T. P. 1991. Allele-specific hypermethylation of the retinoblastoma tumor-suppressor gene. *Am. J. Hum. Genet.* 48: 880–888.
46. Phillips, S., Barton, C., Lee, S., Morton, D., Wallace, D., Lemoine, N., Neoptolemos, J. 1994. Loss of the retinoblastoma susceptibility gene ($RB_1$) is a frequent early event in prostatic tumorigenesis. *Brit. J. Cancer.* 70: 1252–1257.
47. Lee, W., Isaacs, W., Bova, G., Nelson, W. 1997a. CG island methylation changes near the GSTP1 gene in prostatic carcinoma cells detected using the polymerase chain reaction: a new prostate cancer biomarker. *Cancer Epidemiology, Biomarkers & Prevention.* 6: 443–450.
48. Nelson, J., Lee, W—H., Nguyen, S., Jarrard, D., Brooks, J., Magnuson, S., Opgenorth, T., Nelson, W,. Bova, G. 1997. Methylation of the 5'CpG island of the endothelin B receptor gene is common in human prostate cancer. *Cancer Res.* 57:35–37.
49. Lou, W., Krill, D., Dhir, R., Becich, M., Dong, J-T., Frierson, H., Jr., Isaacs, W., Isaacs, J., and Gao, A. C. 1999. Methylation of the CD44 metastasis suppressor gene in human prostate cancer. *Cancer Res.* 59: 2329–2331.
50. Issa, J.-P., Vertino, P., Wu, J., Sazawal, S., Celano, P., Nelkin, B., Halmilton, S., Baylin, S. 1993. Increased cytosine DNA-methyltransferase activity during colon cancer. *J. National Cancer Institute.* 85: 1235–1239.
51. Laird, P., Jackson-Grusby, L., Fazeli, A., Dickinson, S., Jung, W., Li, E., Weinberg, R., Jaenisch, R. 1995. Suppression of intestinal neoplasia by DNA hypomethylation. *Cell.* 81: 197–205.
52. De Marzo, A., Marchi, V., Yang, E., Veeraswamy, R., Lin, X., and Nelson, W. 1999. Abnormal regulation of DNA methyltransferase expression during colorectal carcinogenesis. *Cancer Res.* 59:3855–3860.
53. Toyota, M., Ahuja, N., Suzuki, H., Itoh, F., Ohe-Toyota, M., Imai, K., Baylin, S., and Issa, J-P. 1999. Aberrant methylation in gastric cancer associated with the CpG Island methylator phenotype. *Cancer Res.* 59: 5438–5442.

54. Lombardi, D., Geradts, J., Foley, J., Chiao, C., Lamb, P., and Barrett, J. 1999. Loss of KAI1 expression in the progression of colorectal cancer. *Cancer Res.* 59:5724–5731.
55. Belinsky, S., Nikula, K., Baylin, S., Issa, J.-P. 1996. Increased cytosine DNA-methyltransferase activity in target-cell-specific and an early event in lung cancer. *Proc. Natl. Acad. Sci. USA.* 93: 4045–4050.
56. Esteller, M., Sanchez-Cespedes, M., Rosell, R., Sidransky, D., Baylin, S., and Herman, J. 1999. Detection aberrant promoter hypemmethylation of tumor suppressor genes in serum DNA from non-small cell lung cancer patients. *Cancer Res.* 59:67–70.
57. Leung, S., Yuen, S., Chung, L., Chu, K., Chan, A., and Ho, J. 1999. hMLH1 promoter methylation and lack of hMLH1 expression in sporadic gastric carcinomas with high-frequency microsatellite instability. *Cancer Res.* 59:159–164.
58. Ahuja, N., Mohan, A., Li, Q., Stolker, J., Herman, J., Hamilton, S., Baylin, S., and Issa, J-P. 1997. Association between CpG island methylation and microsatellite instability in colorectal cancer. *Cancer Res.* 57:2270–3374.
59. Berry, S., Garces, C., Hwang, H-S., Kunugi, K., Meyers, M., Davis, T., Boothman, D., and Kinsella, T. 1999. hMLH1, mediates 5-Substituted halogenated thymidine analogue cytotoxicity, DNA incorporation, and radiosensitization in human colon cancer cells. *Cancer Res.* 59:1840–1845.
60. Westphal, C., Hoyes, K., Canman, C., Huang, X., Kastan, M., Hendry, J., and Leder, P. 1998. Loss of atm radiosensitizes multiple p53 null tissues. *Cancer Res.* 58:5637–5639.
61. Lin, H., Huber, R., Schlessinger, D., and Morin, J. 1999. Frequent silencing of the GPC3 gene in ovarian cancer cell lines. *Cancer Res.* 59: 807–810.
62. Tseng, J., Kemp, B., Khuri, F., Kurie, J., Lee, J., Zhou, X., Liu, D., Hong, W., and Mao, L. 1999. Loss of Fhit is frequent in stage I non-small cell lung cancer and in the lungs of chronic smokers. *Cancer Res.* 59: 4798–4803.
63. Toyota, M., Ho, C., Ohe-Toyota, M., Baylin, S., and Issa, J-P. 1999. Inactivation of CACNA1G, a T-Type calcium channel gene, by aberrant methylation of its 5'CpG Island in human tumors. *Cancer Res.* 59: 4535–4541.
64. Devereux, T., Horikawa, I., Anna, C., Anna, L., Afshari, C., Barrett, J. 1999. DNA methylation analysis of the promoter region of the human telomerase reverse transcriptase (hTERT) gene. *Cancer Res.* 59:6087–6090.
65. Widschwendter, M., Berger, J., Daxenbichler, G., Miiller-Holzner, E., Widschwendter, A., Mayr, A., Marth, C., and Zeimet, A. 1997. Loss of retinoic acid receptor β expression in breast cancer and morphologically normal adjacent tissue but not in the normal breast tissue distant from the cancer. *Cancer Res.* 57:4158–4161.
66. Barletta, J., Rainier, S., and Feinberg, A. 1997. Reversal of loss of imprinting in tumor cells by 5-Aza-2'-deoxycytidine. *Cancer Res.* 57:48–50.
67. Cameron, E., Bachman, K., Myohanen, S., Herman, J., and Baylin, S. 1999. Synergy of demethylation and histone deacetylase inhibition in the re-expression of genes silenced in cancer. *Nature Genet* 21:103.
68. Glick, R., Swendeman, S., Coffey, D., Rifkind, R., Marks, P., Richon, V., and La Quaglia, M. 1999. Hybrid polar histone deacetylase inhibitor induces apoptosis and CD95/CD95 ligand expression in human neuroblastoma. *Cancer Res.* 59:4392–4399.
69. Wang, J., Saunthararajah, Y., Redner, R., and Liu, J. 1999. Inhibitors of histone deacetylase relieve ETO-mediated repression and induce differentiation of AML1-ETO leukemia cells. *Cancer Res.* 59:2766–2769.

TABLE 1

The Standard Protocol (StP) indicating the bolus doses of i.p. administered drugs and the schedule of the administration of the drugs and radiation. This protocol was followed for 3 to 5 weeks as indicated in Table 2.
PALA N-(Phosphonacetyl)-L-aspartate; FdC; 5-fluoro-2'-deoxycytidine; CldC: 5-chloro-2'-deoxycytidine; H4U: tetrahydrouridine.

Schedule Table

| Time | MON | TUES | WED | THURS | FRI |
|---|---|---|---|---|---|
| 9 AM | PALA (70)* | FdC + H₄U (7) (25) | CldC + H₄U (150) (25) | CldC + H₄U (125) (25) | |
| 1 PM | FdC + H₄U (7) (25) | | | | Radiation |
| 3 PM | | | Radiation | Radiation | |
| 4 PM | | CldC + H₄U (180) (25) | | | |
| 5 PM | CldC + H₄U (180) (25) | | | | |

*(mg/kg)

TABLE 2

A summary of the final results of the five experiments obtained with two human prostate tumors, a human lung tumor, a human glioblastoma and a human breast tumor with regard to three endpoints. The mice were followed for a minimum of 7 months. Also shown are the results of an additional experiment utilizing 5-iododeoxyuridine and modified protocols with PC3, the human prostate tumor.

| Tumor, Condition of Irradiation | Condition | No. of tumors | Days to reach 4 × initial volume | Days in tumor regrowth delay | Fraction of cures |
|---|---|---|---|---|---|
| No. | Control | 5 | 14 | 0 | 0 |
| Gy, Fractions, Weeks | StP* | 6 | 28 | 0 | 0 |
| •Prostate, PC-3 | X-ray | 9 | 72 | 42 | 0 |
| 47, 11, 4 | StP + X-ray | 10 | 116*/124** | 85*/>97** | 1/10 |
| | Full[b], No PALA | 5 | 104/>142 | 56/>113 | 2/5 |
| •Prostate, H1579 | Control | 5 | 13 | 0 | 0 |
| 43, 11, 4 | StP | 4 | 45 | 2 | 0 |

TABLE 2-continued

A summary of the final results of the five experiments obtained with two human prostate tumors, a human lung tumor, a human glioblastoma and a human breast tumor with regard to three endpoints. The mice were followed for a minimum of 7 months. Also shown are the results of an additional experiment utilizing 5-iododeoxyuridine and modified protocols with PC3, the human prostate tumor.

| Tumor, Condition of Irradiation | Condition | No. of tumors | Days to reach 4 × initial volume | Days in tumor regrowth delay | Fraction of cures |
|---|---|---|---|---|---|
| Pooled data | X-ray | 8 | 24/>48 | 5/>29 | 1/8 |
|  | StP + X-ray | 7 | 108/>134 | 81/>115 | 2/7 |
| •Glioblastoma | Control | 5 | 3† | 0 | 0 |
| SF295 | StP | 5 | 3† | 0 | 0 |
| 44, 8, ‡3 | X-ray | 8 | 17 | 5 | 0 |
|  | StP + X-ray | 7 | 31/>56 | 21/>51 | 1/7 |
| •Breast, GI101 | Control | 7 | 26 | 0 | 0 |
| 42, 14, ‡5 | StP | 8 | 31 | 0 | 0 |
|  | X-ray | 11 | 83 | 50 | 0 |
|  | StP + X-ray | 11 | 100/>106 | 70/>80 | 1/11 |
| •Lung, H165 | Control | 4 | 12 | 0 | 0 |
| 47, 12, 4 | StP | 3 | 20 | 0 | 0 |
|  | X-ray | 5 | 58 | 32 | 0 |
|  | StP + X-ray | 5 | 89/>133 | 72/>123 | 2/5 |
| Experiment with Modified Protocols ||||||
| oProstate, PC-3 | Control | 4 |  | 0 | 0 |
| 52.5, 15, 5§ | X-ray | 4 |  | 17 | 0 |
|  | StP// + X-ray | 6 |  | 68/>112 | 2/6 |
|  | StP s̄ PALA//,a − X-ray | 6 |  | 29/>86 | 2/6 |
|  | StP c̄ IdU//,b + X-ray | 5 |  | 38 | 0 |
|  | PALA & FdC//,c + X-ray | 5 |  | 25/>60 | 1/5 |
|  | StP c̄ (↑) CldC//,d + X-ray | 5 |  | 25/>130 | 3/5 |

•StP, Standard Protocol (CldC, modulators and schedule as shown in Table 1).
*/**calculations excluding cures/calculations designating cures as >200 days.
†for glioblastoma control and StP only, days to reach 2 × initial volume is shown.
‡3 weeks; 1 Bye; 2 weeks.
§4 weeks, 3 weeks Bye, 1 week.
//no tumor regrowth delay or cures occurred with drugs alone (3 animals/group).
aStP as shown in Table 1 except no PALA on Mondays. Instead, FdC (4 mg/kg) administered both AM and Noon on Mondays and 8 mg/kg instead of 7 mg/kg administered on Tuesdays. $H_4U$ always coadministered with FdC.
bStP c̄ IdU, CldC replaced with IdU. Total dose FdC, 2.4 mg/30 g mouse
cPALA (as in StP) with FdC × $H_4U$ administered as in the StP but, in addition, FdC + $H_4U$ substituted for all CldC + $H_4U$ administrations, FdC dose in weeks 1–5 was 27, 32, 32, 37 and 37 mg/kg; i.e. a total dose of 4.95 mg/30 g mouse compared to 2.1 mg/30 g mouse in the StP.
dStP c̄ (↑) CldC, dose of CldC escalated 9% in weeks 2–4. No PALA, no FdC; CldC + $H_4U$ administered as in the StP, but, in addition, CldC + $H_4U$ substituted for all FdC + $H_4U$ administrations.
(//, b, d. the total dose of CldC, IdU and elevated (↑) CldC was 95, 129 and 184 mg/30 g mouse, respectively.

TABLE 3

PC3 1998
4 weeks on 3 weeks off 1 week on
$H_4U$ 25* always co-administered

| CldC + $H_4U$ Only BC | MON | TUES | WED | THURS |  |
|---|---|---|---|---|---|
| Week | CldC | CldC | CldC | CldC | Total |
| I AM | 150* | 225 | 180 | 150 |  |
| PM | 150 | 180 |  |  | 1035 |
| II AM | 150 | 225 | 225 | 180 |  |
| PM | 180 | 200 |  |  | 1160 |
| III AM | 150 | 225 | 250 | 200 |  |
| PM | 200 | 220 |  |  | 1245 |
| IV AM | 150 | 225 | 275 | 225 |  |
| PM | 225 | 250 |  |  | 1350 |
| VIII AM | 150 | 225 | 275 | 225 |  |
| PM | 225 | 250 |  |  | 1350 |

*mg/kg   3.5 Gy in 15 fractions   6,140* CldC
Total Dose: 52.5 Gy   184.4 mg/30 g mouse

What is claimed is:

1. A method of treating at least one tumor in a subject in need of said treatment, wherein the tumor is a member selected from the group consisting of a tumor of the breast, lung, brain, liver, kidney, ovary, uterus, testis, pancreas, gastrointestinal tract, head and neck, nasopharynx, skin, and prostate, and an orofacial tumor, comprising the following steps:

(A) administering a tumor-treating effective amount of an agent to the subject, wherein the agent comprises 5-chloro-2'-deoxycytidine, 4-N-methyl FdC and a cytidine deaminase inhibitor; and (B) exposing the subject to a tumor-treating effective amount of radiation.

2. The method of claim 1, wherein said agent is administered in a slow release formulation.

3. The method of claim 1, wherein the cytidine deaminase inhibitor is tetrahydrouridine, deoxytetrahydrouridine, a pyrimidin-2-one nucleoside, a F pyrimidin-2-one nucleoside, a diazepin-2-1-nucleoside, 1-(2-Deoxy-2-fluoro-β-D arabinofuranosyl)-1,2-dihydropyrimidin-2-one, 2'-Deoxy-2'-F-arazebularine, diazoepinone, 4-hydromethyl-2-oxopyrimidin-2-one nucleoside, or 2'-fluoro-2'-deoxyarabinosyl-tetrahydrouracil.

4. The method of claim 3, wherein the cytidine deaminase inhibitor is tetrahydrouridine or Zebularine.

5. The method of claim 4, wherein the cytidine deaminase inhibitor is tetrahydrouridine.

6. The method of claim 1, wherein said subject is a human.

7. The method of claim 1, wherein the radiation is selected from the group consisting of radiation from protons as a radiation source, radiation from a radiation source implanted proximal to the tumor, radiation from a radionuclide attached to monoclonal antibodies, radiation in a gamma knife, 3D conformal radiation, and radiation in steriotactic radiosurgery.

8. The method of claim 7, wherein said radiation source implanted proximal to the tumor comprises yttrium 90 needles or indium needles.

9. The method of claim 7, wherein said radionuclide is yttrium 90.

10. A method of treating at least one tumors in a subject in need of said treatment, wherein the tumor is a member selected from the group consisting of a tumor, of the breast, lung, brain, liver, kidney, ovary, uterus, testis, pancreas, gastrointestinal tract, head and neck, nasopharynx, skin, and prostate, and an orofacial tumor comprising the following steps:
(A) administering a tumor-treating effective amount of an agent to the subject, wherein the agent comprises 5-chloro-2'-deoxycytidine, 4-N-methyl FdC and a cytidine deaminase inhibitor; and
(B) administering bisulfite to the subject, and thereafter
(C) exposing the subject to a tumor-treating effective amount of radiation.

11. The method of claim 10, further comprising administering cysteine to the subject before exposing the subject to radiation.

12. A method of treating a tumor or tumors in a subject in need of said treatment, wherein the tumor is a member selected from the group consisting of a tumor of the breast, lung, brain, liver, kidney, ovary, uterus, testis, pancreas, gastrointestinal tract, head and neck, nasopharynx, skin, and prostate, and an orofacial tumors, comprising the following steps:
(A) exposing the subject to an amount of radiation sufficient to induce increased deoxycytidine kinase (dCK) and/or increased thymidine kinase (TK) activity in target cells in the tumor or tumors; and then
(B) administering a tumor-treating effective amount of an agent to the subject, wherein the agent comprises 5-chloro-2'-deoxycytidine, 4-N-methyl FdC and a cytidine deaminase inhibitor; and
(C) exposing the subject to a tumor-treating effective amount of radiation.

13. A method of hypomethylating genes in a subject having a tumor resulting from at least one hypermethylated gene, wherein the tumor is a member selected from the group consisting of a tumor of the breast, lung, brain, liver, kidney, ovary, uterus, testis, pancreas, gastrointestinal tract, head and neck, nasopharynx, skin, and prostate, and an orofacial tumor, comprising administering a gene-hypomethylating agent to the subject in an amount effective to hypomethylate said at least one hypermethylated gene, wherein said agent comprises
5-chloro-2'-deoxycytidine, 4-N-methyl FdC and a cytidine deaminase inhibitor.

14. The method of claim 13, wherein the cytidine deaminase inhibitor is tetrahydrouridine, deoxytetrahydrouridine, a pyrimidin-2-one nucleoside, a F pyrimidin-2-one nucleoside, a diazepin-2-1-nucleoside, 1-(2-Deoxy-2-fluoro-β-D arabinofuranosyl)-1,2-dihydropyrimidin-2-one, 2'-Deoxy-2'-F-arazebularine, diazoepinone, 4-hydromethyl-2-oxopyrimidin-2-one nucleoside, or 2'-fluoro-2'-deoxyarabinosyl-tetrahydrouracil.

15. The method of claim 14, wherein the cytidine deaminase inhibitor is tetrahydrouridine or Zebularine.

16. The method of claim 15, wherein the cytidine deaminase inhibitor is tetrahydrouridine.

17. The method of claim 13, wherein said subject is a human.

18. The method of claim 13, further comprising exposing the subject to a tumor-treating effective amount of radiation, wherein the agent hypomethylates genes silenced in a tumor to reduce (A) the aggressiveness of the tumor, (B) the metastatic propensity of the tumor, (C) the genetic instability of the tumor, and/or (D) the resistance of the tumor to drug or radiation treatment.

19. A method of preparing a medication for sensitization of at least one tumor to radiation treatment in a subject, wherein the tumor is a member selected from the group consisting of a tumor of the breast, lung, brain, liver, kidney, ovary, uterus, testis, pancreas, gastrointestinal tract, head and neck, nasopharynx, skin, and prostate, and an orofacial tumors, wherein said method comprises preparing the medication by
combining 5-chloro-2'-deoxycytidine, 4-N-methyl FdC and a cytidine deaminase inhibitor.

20. A method of preparing a medication for the sensitization of at least one tumor to radiation treatment, wherein the tumor is a member selected from the group consisting of a tumor of the breast, lung, brain, liver, kidney, ovary, uterus, testis, pancreas, gastrointestinal tract, head and neck, nasopharynx, skin, and prostate, and an orofacial tumors, comprising mixing
5-chloro-2'-deoxycytidine, 4-N-methyl FdC and a cytidine deaminase inhibitor.

* * * * *